(12) United States Patent
Swanson et al.

(10) Patent No.: US 10,087,405 B2
(45) Date of Patent: Oct. 2, 2018

(54) WIPE WITH A GUANIDINYL-CONTAINING POLYMER

(71) Applicant: 3M INNOVATIVE PROPERTIES COMPANY, St. Paul, MN (US)

(72) Inventors: Steven P. Swanson, Blaine, MN (US); Jerald K. Rasmussen, Woodville, WI (US); George W. Griesgraber, Eagan, MN (US); Andrew W. Vail, Woodbury, MN (US); Andrew S. Waller, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/896,145

(22) PCT Filed: Jun. 20, 2014

(86) PCT No.: PCT/US2014/043437
§ 371 (c)(1),
(2) Date: Dec. 4, 2015

(87) PCT Pub. No.: WO2014/209798
PCT Pub. Date: Dec. 31, 2014

(65) Prior Publication Data
US 2016/0115430 A1    Apr. 28, 2016

Related U.S. Application Data

(60) Provisional application No. 61/840,537, filed on Jun. 28, 2013.

(51) Int. Cl.
*B08B 7/00* (2006.01)
*C11D 17/04* (2006.01)
(Continued)

(52) U.S. Cl.
CPC .......... *C11D 17/049* (2013.01); *A01N 47/44* (2013.01); *A47L 13/17* (2013.01); *B08B 1/006* (2013.01); *B08B 1/00* (2013.01)

(58) Field of Classification Search
CPC ......... C11D 17/049; B08B 1/006; B08B 1/00; A47L 13/17; A01N 47/44
See application file for complete search history.

(56) References Cited

U.S. PATENT DOCUMENTS

| 4,565,783 A | 1/1986 | Hansen |
|---|---|---|
| 5,089,413 A | 2/1992 | Nelson |

(Continued)

FOREIGN PATENT DOCUMENTS

| JP | 2-61000 | 3/1990 |
|---|---|---|
| JP | 2002-113082 | 4/2002 |

(Continued)

OTHER PUBLICATIONS

Hill, "General acid-catalyzed addition of anilines to dicyanamide ion through a concerted mechanism", Journal of Organic Chemistry, 1984, vol. 49, pp. 1819-1823.

(Continued)

*Primary Examiner* — Sharidan Carrillo
(74) *Attorney, Agent, or Firm* — Adrian L. Pishko

(57) ABSTRACT

A wipe article includes a substrate, a cationic coating disposed on a surface of the substrate, distributed throughout the substrate, or both. The cationic coating contains a guanidinyl-containing polymer that is crosslinked and bound to the substrate. The substrate includes sponge, non-woven fabric, or woven fabric. The wipes are useful for removing microorganisms from a microorganism-contaminated surface and also for reducing re-contamination of the cleaned surface or transfer to another surface of the removed microorganisms.

13 Claims, 2 Drawing Sheets

(51) Int. Cl.
*A01N 47/44* (2006.01)
*A47L 13/17* (2006.01)
*B08B 1/00* (2006.01)

(56) References Cited

U.S. PATENT DOCUMENTS

| | | |
|---|---|---|
| 5,141,803 A | 8/1992 | Pregozen |
| 5,232,838 A | 8/1993 | Nelson |
| 5,712,027 A | 1/1998 | Ali |
| 6,033,719 A | 3/2000 | Keogh |
| 6,294,163 B1 | 9/2001 | Dhal |
| 6,617,142 B2 | 9/2003 | Keogh |
| 7,094,743 B2 | 8/2006 | Thioliere |
| 7,101,621 B2 | 9/2006 | Haddad |
| 7,422,868 B2 | 9/2008 | Fan |
| 8,377,672 B2 | 2/2013 | Rasmussen |
| 8,435,776 B2 | 5/2013 | Rasmussen |
| 2003/0216272 A1 | 11/2003 | Sherry |
| 2004/0009141 A1 | 1/2004 | Koenig |
| 2005/0025668 A1 | 2/2005 | Katsigras |
| 2005/0136082 A1 | 6/2005 | Soane |
| 2005/0137540 A1 | 6/2005 | Villanueva |
| 2006/0051385 A1 | 3/2006 | Scholz |
| 2007/0042198 A1 | 2/2007 | Schonemyr |
| 2007/0048356 A1 | 3/2007 | Schorr |
| 2007/0134337 A1 | 6/2007 | Villanueva |
| 2007/0142262 A1 | 6/2007 | Sayre |
| 2008/0139441 A1* | 6/2008 | Xiao .......... A01N 47/44 510/319 |
| 2009/0226394 A1 | 9/2009 | Champ |
| 2010/0075560 A1 | 3/2010 | Seshadri |
| 2010/0111811 A1 | 5/2010 | Gadkaree |
| 2010/0323895 A1 | 12/2010 | Garner |
| 2011/0201078 A1 | 8/2011 | Rasmussen |
| 2011/0217752 A1 | 9/2011 | Rasmussen |
| 2012/0207805 A1 | 8/2012 | Colman |
| 2012/0252091 A1 | 10/2012 | Rasmussen |
| 2013/0217032 A1* | 8/2013 | Rasmussen .......... C08G 69/10 435/7.1 |
| 2016/0115430 A1* | 4/2016 | Swanson .......... A47L 13/17 134/6 |

FOREIGN PATENT DOCUMENTS

| | | |
|---|---|---|
| JP | 2003-095815 | 4/2003 |
| JP | 2004-269518 | 9/2004 |
| JP | 2011-507610 | 3/2011 |
| WO | WO 2007-027904 | 3/2007 |
| WO | WO 2007-101445 | 9/2007 |
| WO | 2009/085570 | 7/2009 |
| WO | WO 2011-103106 | 8/2011 |
| WO | WO 2011-163070 | 12/2011 |
| WO | WO 2013-184366 | 12/2013 |

OTHER PUBLICATIONS

Katritzky, Comprehensive Organic Functional Group Transformation, vol. 6, p. 640.
Rasmussen, "Crosslinked, Hydrophilic, Azlactone-Functional Polymeric Beads: A Two-Step Approach", Reactive Polymers, 1991/1992, vol. 16, pp. 199-212.
Rose, "Bisdiguanides having antibacterial activity", Journal of the Chemical Society, 1956, pp. 4422-4425.
Suominen, Cellulose wipe product data sheet, 1 pg.
Wente, "Manufacture of Superfine Organic Fibers", Naval Research Laboratories Report No. 4364, 1954, 23pgs.
Wente, "Superfine Thermoplastic Fibers", Industrial and Engineering Chemistry, 1956, vol. 48, pp. 1342-1346.
Williams, Gareth J., Cardiff University, "Determining the ability of surface wipes to remove, kill and prevent the transfer of *Staphylococcus aureus* from contaminated surfaces," 2 pages.
International Search Report for PCT International Application No. PCT/US2014/043437, dated Nov. 5, 2014, 4pgs.
Sattar, et al., "The crucial role of wiping in decontamination of high-touch environmental surfaces: Review of current status and directions for the future," American Journal of Infection Control, vol. 41, (2013) pp. S97-S104.
Siani, et al., "Efficacy of 'sporicial' wipes against Clostridium difficile," American Journal of Infection Control, vol. 39, No. 3, Apr. 2011, pp. 212-218.
Williams, et al., "Limitations of the Efficacy of Surface Disinfection in the Healthcare Setting," Infection Control and Hospital Epidemiology, vol. 30, No. 6, Jun. 2009, pp. 570-573.
Williams, et al., "The development of a new three-step protocol to determine the efficacy of disinfectant wipes on surfaces contaminated with *Staphylococcus aureus*," Journal of Hospital Infection, vol. 67, (2007), pp. 329-335.

* cited by examiner

WIPE WITH A GUANIDINYL-CONTAINING POLYMER

CROSS REFERENCE TO RELATED APPLICATIONS

This application is a national stage filing under 35 U.S.C. 371 of PCT/US2014/043437, filed Jun. 20, 2014, which claims priority to U.S. Application No. 61/840,537, filed Jun. 28, 2013, the disclosure of which is incorporated by reference in its/their entirety herein.

TECHNICAL FIELD

The present disclosure is directed to a wipe having a cationic coating that contains a guanidinyl-containing polymer. Methods of using the wipe and methods of making the wipe are also disclosed.

BACKGROUND

Microbial contamination can be a problem in many fields of activity. Unwanted microbial populations can be a health hazard, can cause problems in pharmaceutical and food production, and can cause waste due to the harmful effects of such bioactive microbial contamination on sensitive compositions and materials. Many surfaces can contain a microbial residue of sufficiently high numbers to contaminate a sensitive product or process. Elimination or removal of such microbial residue is a desired end.

In the healthcare industry it is a common practice to clean and/or disinfect environmental surfaces, medical instruments and devices to enhance hygiene and patient safety. Effective disinfection must act against a broad spectrum of microorganisms including those resistant to common antibacterial agents. However, some high level disinfectants used for the eradication of these resistant microorganisms are corrosive to medical instruments and surfaces.

In the past, sponges, woven and nonwoven fabric and similar materials have been used as wipes and have been combined with solvent or small molecule chemistry to obtain microbial removal and micro-biocidal or static growth characteristics. Although these wipes might all have useful physical attributes, a substantial need exists in the art to obtain removal of harmful microbial populations from surfaces, with little or no risk of re-contamination or re-deposition from the wipe.

SUMMARY

The present disclosure is directed to a wipe that contains a cationic coating, to methods of making the wipe, and to methods of using the wipe. The cationic coating includes a guanidinyl-containing polymer that is crosslinked, or that is covalently attached to the substrate, or both crosslinked and covalently attached to the substrate. The coating is not easily separated from the substrate. As a result, minimal or no residue of the cationic coating is left on surfaces after being cleaned by the wipes.

The wipes are useful for removing microorganisms from a microorganism-contaminated surface and also for reducing re-contamination of the cleaned surface with the removed microorganism or transfer of the removed microorganisms to another surface. Advantageously, when contacted with an area of a microorganism-contaminated surface, the wipes can remove at least 99 percent of the microorganisms in the area. The removed microorganisms are attached to the wipe and no more than 0.2 percent of the removed microorganisms are transferred from the wipe to a second surface when the wipes are contacted with a second surface or with the previously cleaned surface.

In a first aspect, a wipe is provided that includes (a) a substrate comprising a sponge, a woven fabric, or a nonwoven fabric and (b) a cationic coating disposed on a surface of the substrate, distributed throughout at least a portion of the substrate, or both. The cationic coating contains a guanidinyl-containing polymer that is crosslinked, covalently attached to the substrate, or both. When the wipe is contacted in the presence of a liquid with an area of a microorganism-contaminated surface, at least 99 percent of microorganisms present on the microorganism-contaminated surface are removed from the area by the wipe, and wherein the wipe, when contacted in the presence of the liquid with the area of the microorganism-contaminated surface and then contacted with a second surface, transfers no more than 0.2 percent of the microorganisms from the wipe to the second surface.

In a second aspect, a method of removing microorganisms from a microorganism-contaminated surface is provided. The method includes preparing a wipe that includes (a) a substrate comprising a sponge, a woven fabric, or a nonwoven fabric and (b) a cationic coating disposed on a surface of the substrate, distributed throughout at least a portion of the substrate, or both. The cationic coating contains a guanidinyl-containing polymer that is crosslinked, covalently attached to the substrate, or both. The method further includes contacting the wipe in the presence of a liquid with an area of the microorganism-contaminated surface, wherein at least 99 percent of microorganisms present on the microorganism-contaminated surface are removed from the area by the wipe, and wherein the wipe, when contacted in the presence of the liquid with the area of the microorganism-contaminated surface and then contacted with a second surface, transfers no more than 0.2 percent of the microorganisms from the wipe to the second surface.

Other features and aspects of the wipes, methods of making the wipes, and methods of using the wipes are set forth in greater detail below.

DETAILED DESCRIPTION

The coated wipe includes a substrate and a cationic coating bound to the substrate. The cationic coating includes a guanidinyl-containing polymer that is crosslinked, covalently attached to the substrate, or both. The wipe is useful, for example, for effective removal of such contaminants as microorganisms from a microorganism-contaminated surface and for minimal transfer of the removed microorganisms to another surface or to a previously cleaned surface.

As used herein, "polymer" is inclusive of a homopolymer, copolymer, terpolymer, and the like.

As used herein, "(meth)acrylic" is inclusive of both methacrylic and acrylic. Likewise, the term "(meth)acrylamide" refers to both methacrylamide and acrylamide and the term "(meth)acrylate refers to both methacrylate and acrylate.

As used herein, "wet-contacting" and "contacting in the presence of a liquid" are used interchangeable and generally refer to contacting a wipe with a surface (e.g., a microorganism-contaminated surface such as a surface contaminated with microorganisms), wherein the wipe and/or the surface is wet with a liquid at an area where the surface and the wipe come into contact with each other. The liquid typically includes at least 10 weight percent water and can include up to 100 weight percent water, relative to a total weight of the liquid.

As used herein, the term "bound" or "binding" in reference to the cationic coating (e.g., the guanidinyl-containing polymer in the cationic coating) being bound to the substrate or binding the cationic coating to the substrate means that the cationic coating cannot be removed without destroying the substrate. The cationic coating can be chemically attached to the substrate or can be crosslinked around the fibers of the substrate such that the coating cannot be removed by peeling, dissolving in water or an organic solvent.

The term "microorganism" refers to bacteria (including gram-positive bacteria and gram-negative bacteria), fungi (e.g., yeasts), molds, protozoans, viruses (including both non-enveloped and enveloped viruses), bacterial endospores, and the like, and combinations thereof. In some embodiments, the microorganisms include bacterial endospores.

Figure 1:
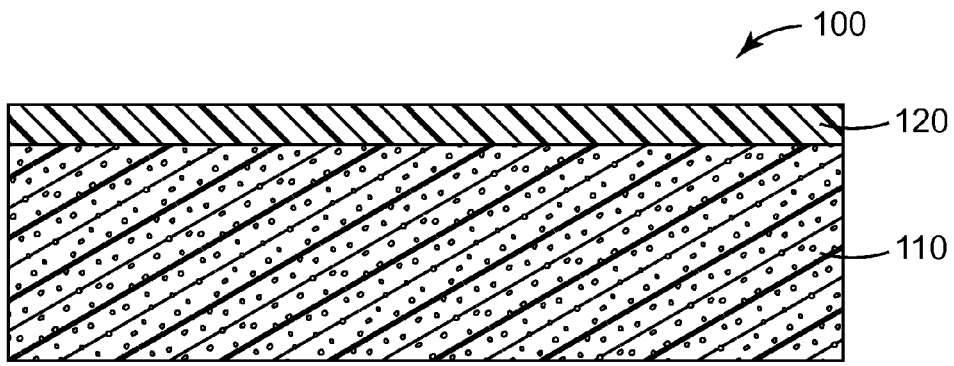
FIGS. 1 to 3 are schematic profile views of exemplary wipes.
Figure 2:
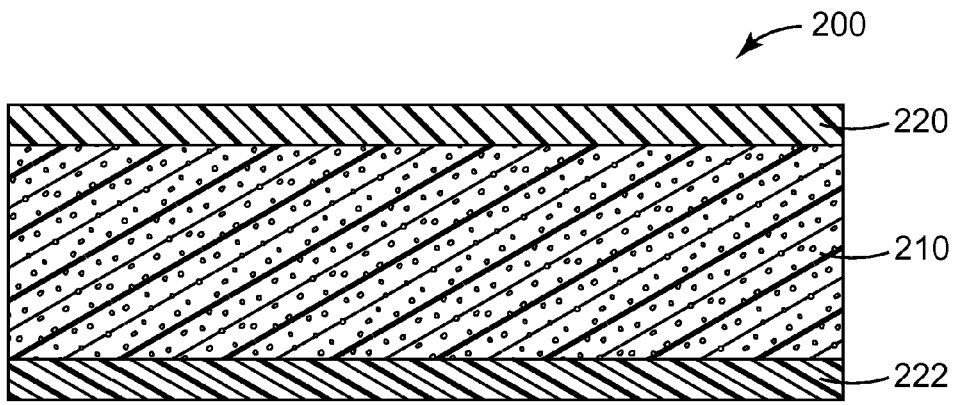
Figure 3:
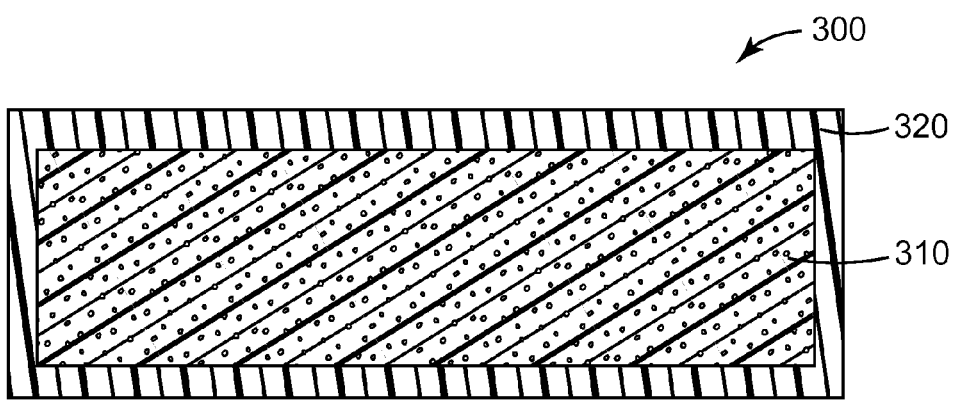

FIG. 1 is a schematic profile view of an exemplary embodiment of a wipe 100 having a substrate 110 and a cationic coating layer 120 disposed on a surface of the substrate. FIG. 2 shows another exemplary embodiment of a wipe 200 that includes a substrate 210 and a cationic coating layer 220 disposed on a first major surface of substrate 210. Wipe 200 further includes a coating layer 222 disposed on a second major surface of substrate layer 210 opposite the first major surface of substrate 210. In some embodiments, coating layer 222 can include the same cationic coating composition used in cationic coating layer 220, although this is not a requirement, and coating layer 222 can alternatively include other coating compositions. FIG. 3 shows an exemplary embodiment of a coated wipe 300 having a cationic coating layer 320 surrounding a substrate 310. The figures are not drawn to scale.

In some other embodiments (not shown), a cationic coating can be disposed on a surface of a substrate, as well as being distributed through at least a portion of the substrate. That is, the cationic coating can penetrate into the substrate. For example, if the substrate is a sponge, the cationic coating may be on a surface of substrate and can be distributed throughout all or any portion of the substrate. In other examples, if the substrate includes fiber, the cationic coating can surround the fibers or any portion of the fibers.

The cationic coating includes a guanidinyl-containing polymer. The guanidinyl group can be located at any position in the polymer. In most embodiments, the guanidinyl group is part of a pendant group attached to the backbone of the polymer. In some embodiments, however, the guanidinyl group is part of backbone of the polymer. As used herein, the term "guanidinyl" refers to a group of the formula —NR$^3$—C(=NR$^4$)—NR$^4$R$^5$. If the guanidinyl group is part of a pendant group, the group R$^3$ refers to hydrogen, C$_1$-C$_{12}$ (hetero)alkyl, or C$_5$-C$_{12}$ (hetero)aryl. If the guanidinyl group is part of the backbone of the polymer, the group R$^3$ can refer to a residue of a polymer chain. Each group R$^4$ is independently hydrogen, C$_1$-C$_{12}$ (hetero)alkyl, or C$_5$-C$_{12}$ (hetero)aryl. Group R$^5$ is hydrogen, C$_1$-C$_{12}$ (hetero)alkyl, C$_5$-C$_{12}$ (hetero)aryl, or a group of formula —N(R$^4$)$_2$. The guanidinyl group can be part of a biguanidinyl group that is of formula —NR$^3$—C(=NR$^4$)—NR$^4$—C(=NR$^4$)—NR$^4$R$^5$ where the groups R$^3$, R$^4$, and R$^5$ are the same as defined above.

As used herein, "alkyl" refers to a monovalent radical of an alkane and includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like.

As used herein, "alkylene" refers to a divalent radical of an alkane and includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methylene, ethylene, n-propylene, n-butylene, n-pentylene, isobutylene, t-butylene, isopropylene, n-octylene, n-heptylene, ethylhexylene, cyclopentylene, cyclohexylene, cycloheptylene, adamantylene, and norbornylene, and the like.

As used herein, "aryl" is a monovalent radical of an aromatic group containing 5-12 ring atoms and can contain optional fused rings, which may be saturated, unsaturated, or aromatic. Examples of an aryl groups that are carbocyclic include phenyl, naphthyl, biphenyl, phenanthryl, and anthracyl. The term "heteroaryl" refers to an aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. The term "(hetero)aryl" refers to both aryl and heteroaryl groups.

As used herein, "arylene" is a divalent radical of an aromatic group containing 5-12 ring atoms and can contain optional fused rings, which may be saturated, unsaturated, or aromatic. Examples of an arylene groups that are carbocyclic include phenylene, naphthylene, biphenylene, phenanthrylene, and anthracylene. The term "heteroarylene" refers to an arylene containing 1-3 heteroatoms such as nitrogen, oxygen, or sulfur and can contain fused rings. Some examples of heteroarylene groups are pyridylene, furanylene, pyrrolylene, thienylene, thiazolylene, oxazolylene, imidazolylene, indolylene, benzofuranylene, and benzthiazolylene. The term "(hetero)arylene" refers to both arylene and heteroarylene.

Although any guanidinyl-containing polymer can be used in the cationic coating, this polymer is often of Formula (I).

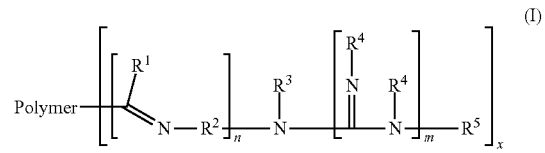

In Formula (I), the group R$^1$ is hydrogen, C$_1$-C$_{12}$ (hetero)alkyl, or C$_5$-C$_{12}$ (hetero)aryl, or a residue of the polymer chain. The group R$^2$ is a covalent bond, a C$_2$-C$_{12}$ (hetero)alkylene, or a C$_5$-C$_{12}$ (hetero)arylene. The group R$^3$ is H, C$_1$-C$_{12}$ (hetero)alkyl, or C$_5$-C$_{12}$ (hetero)aryl, or can be a residue of the polymer chain when n is 0. Each group R$^4$ is independently hydrogen, $C_1$-$C_{12}$ (hetero)alkyl, or $C_5$-$C_{12}$ (hetero)aryl. The group $R^5$ is hydrogen, $C_1$-$C_{12}$ (hetero)alkyl, $C_5$-$C_{12}$ (hetero)aryl, or —$N(R^4)_2$. The variable n is equal to 0 or 1 depending on the precursor polymer used to form the guanidinyl-containing polymer. The variable m is equal to 1 or 2 depending on whether the cationic group is a guanidinyl or biguanidinyl group. The term "Polymer" in Formula (I) refers to all portions of the guanidinyl-containing polymer except the x groups of formula —[C($R^1$)=N—$R^2$—]$_n$N($R^3$)—[C(=N$R^4$)—N$R^4R^5$—]$_m$. The term x is a variable equal to at least 1.

Most guanidinyl-containing polymers have more than one guanidinyl group. The number of guanidinyl groups can be varied depending the method used to prepare the guanidinyl-containing polymer. For example, the number of guanidinyl groups can depend on the choice of precursor polymer selected for reacting with a suitable guanylating agent. In some embodiments, the variable x can be up to 1000, up to 500, up to 100, up to 80, up to 60, up to 40, up to 20, or up to 10.

The guanidinyl-containing polymer of Formula (I) is often the reaction product of (a) a precursor polymer and (b) a suitable guanylating agent. The precursor polymer is often an amino-containing polymer or a carbonyl-containing polymer. When the precursor polymer is an amino-containing polymer, the variable n in Formula (I) is typically equal to 0. When the precursor polymer is a carbonyl-containing polymer, the variable n is equal to 1. If the guanylating agent contains a guanidinyl group or a precursor of a guanidinyl group, the variable m in Formula (I) is equal to 1. If the guanylating agent contains a biguanidinyl group or a precursor of a biguanidinyl group, the variable m in Formula (I) is equal to 2.

In embodiments where n is 0, the base polymer of the guanidinyl-containing polymer is often prepared by reaction of a suitable guanylating agent and an amino-containing polymer. In other embodiments, where n is 1, the guanidinyl-containing polymer is often prepared by reaction of a suitable guanylating agent and a carbonyl-containing polymer.

In those embodiments where n is 0 and the precursor polymer is an amino-containing polymer, the structure of the guanidinyl-containing polymer of Formula (I) can also be written more simply as the structure of Formula (II).

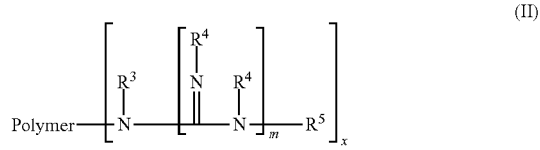

(II)

In Formula (II), the group $R^3$ is hydrogen, $C_1$-$C_{12}$ (hetero)alkyl, or $C_5$-$C_{12}$ (hetero)aryl, or can be a residue of the polymer chain. When the guanidinyl group is part of a pendant group, $R^3$ is hydrogen, $C_1$-$C_{12}$ (hetero)alkyl, or $C_5$-$C_{12}$ (hetero)aryl. Each $R^4$ is independently hydrogen, $C_1$-$C_{12}$ (hetero)alkyl, or $C_5$-$C_{12}$ (hetero)aryl. The group $R^5$ is hydrogen, $C_1$-$C_{12}$ (hetero)alkyl, or $C_5$-$C_{12}$ (hetero)aryl, or —$N(R^4)_2$. The variable m is equal to 1 or 2. The term "Polymer" in Formula (II) refers to all portions of the guanidinyl-containing polymer except the x groups of formula —N($R^3$)—[C(=N$R^4$)—N$R^4R^5$—]$_m$. The term x is a variable equal to at least 1.

The amino-containing polymer used as a precursor polymer to prepare a guanidinyl-containing polymer of Formula (II) can be represented by the formula Polymer —N($R^3$)H. As noted above, however, the amino-containing polymer typically has many groups —N($R^3$)H but Formula (I) shows only one for ease of discussion purposes only. The —N($R^3$)H groups can be a primary or secondary amino group and can be part of a pendant group or part of the backbone of the precursor polymer. The amino-containing polymers can be synthesized or can be naturally occurring biopolymers. Suitable amino-containing polymers can be prepared by chain growth or step growth polymerization procedures with amino-containing monomers. These monomers can also, if desired, be copolymerized with other monomers without an amino-containing group. Additionally, the amino-containing polymers can be obtained by grafting primary or secondary amine groups using an appropriate grafting technique.

In some embodiments, useful amino-containing polymers are polyamines that are water soluble or water-dispersible. As used herein, the term "water soluble" refers to a material that can be dissolved in water. The solubility is typically at least about 0.1 gram per milliliter of water. As used herein, the term "water dispersible" refers to a material that is not water soluble but that can be emulsified or suspended in water.

Examples of amino-containing polymers suitable for use, which are prepared by chain growth polymerization include, but are not limited to, polyvinylamine, poly(N-methylvinylamine), polyallylamine, polyallylmethylamine, polydiallylamine, poly(4-aminomethylstyrene), poly(4-amino styrene), poly(acrylamide-co-methylaminopropylacrylamide), and poly(acrylamide-co-amino ethylmethacrylate).

Examples of amino polymers suitable for use, which are prepared by step growth polymerization include, but are not limited to, polyethylenimine, polypropylenimine, polylysine, polyaminoamides, polydimethylamine-epichlorohydrin-ethylenediamine, and any of a number of polyaminosiloxanes, which can be prepared from monomers such as aminopropyltriethoxysilane, N-(2-aminoethyl)-3-aminopropyltrimethoxysilane, N-trimethoxysilylpropyl-N-methylamine, and bis(trimethoxysilylpropyl)amine.

Other useful amino-containing polymers that have primary or secondary amino end groups include, but are not limited to, dendrimers (hyperbranched polymers) formed from polyamidoamine (PAMAM) and polypropylenimine. Exemplary dendrimeric materials formed from PAMAM are commercially available under the trade designation "STARBURST (PAMAM) dendrimer" (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups) from Aldrich Chemical (Milwaukee, Wis.). Dendrimeric materials formed from polypropylenimine are commercially available under the trade designation "DAB-Am" from Aldrich Chemical. For example, DAB-Am-4 is a generation 1 polypropylenimine tetraamine dendrimer with 4 primary amino groups, DAB-Am-8 is a generation 2 polypropylenimine octaamine dendrimer with 8 primary amino groups, DAB-Am-16 is a generation 3 polypropylenimine hexadecaamine with 16 primary amino groups, DAB-Am-32 is a generation 4 polypropylenimine dotriacontaamine dendrimer with 32 primary amino groups, and DAB-Am-64 is a generation 5 polypropylenimine tetrahexacontaamine dendrimer with 64 primary amino groups.

Examples of suitable amino-containing polymers that are biopolymers include chitosan as well as starch that is grafted with reagents such as methylaminoethylchloride.

Still other examples of amino-containing polymers include polyacrylamide homo- or copolymers and amino-containing polyacrylate homo- or copolymers prepared with a monomer composition containing an amino-containing monomer such as an aminoalkyl(meth)acrylate, (meth)acrylamidoalkylamine, and diallylamine.

For some wipes, the preferred amino-containing polymers include polyaminoamides, polyethyleneimine, polyvinylamine, polyallylamine, and polydiallylamine.

Suitable commercially available amino-containing polymers include, but are not limited to, polyamidoamines that are available under the trade designations ANQUAMINE (e.g., ANQUAMINE 360, 401, 419, 456, and 701) from Air Products and Chemicals (Allentown, Pa.), polyethylenimine polymers that are available under the trade designation LUPASOL (e.g., LUPASOL FG, PR 8515, Waterfree, P, and PS) from BASF Corporation (Resselaer, N.Y.), polyethylenimine polymers such as those available under the trade designation CORCAT P-600 from EIT Company (Lake Wylie, S.C.), and polyamide resins such as those available from Cognis Corporation (Cincinnati, Ohio) under the traded designation VERSAMID series of resins that are formed by reacting a dimerized unsaturated fatty acid with alkylene polyamines.

Guanidinyl-containing polymers can be prepared by reaction of the amino-containing polymer precursor with a guanylating agent. Although all the amino groups of the amino-containing polymer can be reacted with the guanylating agent, there are often some unreacted amino groups from the amino-containing polymer precursor remaining in the guanidinyl-containing polymer. Typically, at least 0.1 mole percent, at least 0.5 mole percent, at least 1 mole percent, at least 2 mole percent, at least 10 mole percent, at least 20 mole percent, or at least 50 mole percent of the amino groups in the amino-containing polymer precursor are reacted with the guanylating agent. Up to 100 mole percent, up to 90 mole percent, up to 80 mole percent, or up to 60 mole percent of the amino groups can be reacted with the guanylating agent. For example, the guanylating agent can be used in amounts sufficient to functionalize 0.1 to 100 mole percent, 0.5 to 90 mole percent, 1 to 90 mole percent, 1 to 80 mole percent, 1 to 60 mole percent, 2 to 50 mole percent, 2 to 25 mole percent, or 2 to 10 mole percent of the amino groups in the amino-containing polymer.

Known guanylating agents for reaction with an amino-containing polymer precursor include, but are not limited to, cyanamide; O-alkylisourea salts such as O-methylisourea sulfate, O-methylisourea hydrogen sulfate, O-methylisourea acetate, O-ethylisourea hydrogen sulfate, and O-ethylisourea hydrochloride; chloroformamidine hydrochloride; 1-amidino-1,2,4-triazole hydrochloride; 3,5-dimethylpyrazole-1-carboxamidine nitrate; pyrazole-1-carboxamidine hydrochloride; N-amidinopyrazole-1-carboxamidine hydrochloride; and carbodiimides such as dicyclohexylcarbodiimide, N-ethyl-N'-(3-dimethylaminopropyl)carbodiimide, and diisopropylcarbodiimide. The amino-containing polymer may also be acylated with guanidino-functional carboxylic acids such as guanidinoacetic acid and 4-guanidinobutyric acid in the presence of activating agents such as EDC (N-[3-(dimethylamino)propyl]-3-ethylcarbodiimide hydrochloride), or EEDQ (2-ethoxy-1-ethoxycarbonyl-1,2-dihydroquinoline). Additionally, the guanidinyl-containing polymer may be prepared by alkylation with chloroacetone guanyl hydrazone, as described in U.S. Pat. No. 5,712,027 (Ali et al.).

Guanylating agents for the preparation of biguanide-containing polymers include sodium dicyanamide, dicyanodiamide and substituted cyanoguanidines such as $N^3$-p-chlorophenyl-N1-cyanoguanidine, $N^3$-phenyl-$N^1$-cyanoguanidine, $N^3$-alpha-naphthyl-$N^1$-cyanoguanidine, $N^3$-methyl-N1-cyanoguanidine, $N^3,N^3$-dimethyl-$N^1$-cyanoguanidine, $N^3$-(2-hydroxyethyl)-$N^1$-cyanoguanidine, and $N^3$-butyl-$N^1$-cyanoguanidine. Alkylene- and arylenebiscyanoguanidines may be utilized to prepare biguanide functional polymers by chain extension reactions. The preparation of cyanoguanidines and biscyanoguanidines is described in detail in Rose, F. L. and Swain, G. J. Chem Soc., 1956, pp. 4422-4425. Other useful guanylating reagents are described by Alan R. Katritzky et al., Comprehensive Organic Functional Group Transformation, Vol. 6, p. 640.

The guanidinyl-containing polymer formed by reaction of an amino-containing polymer precursor and a guanylating agent will have pendent or catenary guanidinyl groups of the Formula (III).

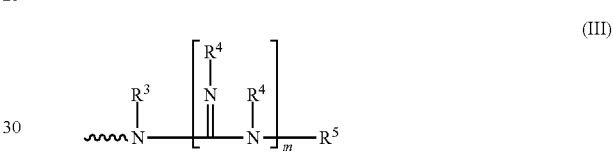

In Formula (III), the groups $R^3$, $R^4$, and $R^5$ and the variable m are the same as defined above. The wavy line attached to the $N(R^3)$ group shows the position of attachment the group to the rest of the polymeric material. In most embodiments, the group of Formula (III) is in a pendant group of the guanidinyl-containing polymer.

In some embodiments, it may be advantageous to react the amino-containing polymer precursor to provide other ligands or groups in addition to the guanidinyl-containing group. For example, it may be useful to include a hydrophobic ligand, an ionic ligand, or a hydrogen bonding ligand. This can be particularly advantageous for the removal of certain microorganisms during the wiping of a microorganism-contaminated surface.

The additional ligands can be readily incorporated into the amino-containing polymers by alkylation or acylation procedures well known in the art. For example amino groups of the amino-containing polymer can be reacted using halide, sulfonate, and sulfate displacement reactions or using epoxide ring opening reactions. Useful alkylating agents for these reactions include, for example, dimethylsulfate, butyl bromide, butyl chloride, benzyl bromide, dodecyl bromide, 2-chloroethanol, bromoacetic acid, 2-chloroethyltrimethylammonium chloride, styrene oxide, glycidyl hexadecyl ether, glycidyltrimethylammonium chloride, and glycidyl phenyl ether. Useful acylating agents include, for example, acid chlorides and anhydrides such as benzoyl chloride, acetic anhydride, succinic anhydride, and decanoyl chloride, and isocyanates such as trimethylsilylisocyanate, phenyl isocyanate, butyl isocyanate, and butyl isothiocyanate. In such embodiments 0.1 to 20 mole percent, preferably 2 to 10 mole percent, of the available amino groups of the amino-containing polymer may be alkylated and/or acylated.

The guanidinyl-containing polymer can be crosslinked. The amino-containing polymer can be crosslinked prior to reaction with the guanylating agent. Alternatively, the guanidinyl-containing polymer can be crosslined by reaction of a crosslinker with remaining amino groups from the amino-containing polymer precursor or with some of the guanidinyl groups. Suitable crosslinkers include amine-reactive compounds such as bis- and polyaldehydes such as glutaraldehyde, bis- and polygylcidylethers such as butane-dioldiglycidylether and ethyleneglycoldiglycidylether, polycarboxylic acids and their derivatives (e.g., acid chlorides), polyisocyanates, formaldehyde-based crosslinkers such as hydroxymethyl and alkoxymethyl functional crosslinkers, such as those derived from urea or melamine, and amine-reactive silanes, such as 3-glycidoxypropyltrimethoxysilane, 3-glycidoxypropyltriethoxysilane, 5,6-epoxyhexyltriethoxysilane, (p-chloromethyl)phenyltrimethoxysilane, chloromethyltriethoxysilane, 3-isocyanatopropyltriethoxysilane, and 3-thiocyanatopropyltriethoxysilane.

In other embodiments, the guanidinyl-containing polymer is of Formula (IV), which corresponds to Formula (I) where n is equal to 1.

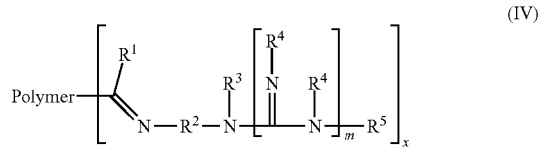

In Formula (IV), the group $R^1$ is hydrogen, $C_1$-$C_{12}$ (hetero)alkyl, or $C_5$-$C_{12}$ (hetero)aryl, or a residue of the polymer chain. If the guanidinyl-containing group is the reaction product of a guanylating agent and a carbonyl group that is part of the backbone of the polymer, $R^1$ is a residue of the polymer chain. Group $R^2$ is a covalent bond, a $C_2$-$C_{12}$ (hetero)alkylene, or a $C_5$-$C_{12}$ (hetero)arylene. Group $R^3$ is hydrogen, $C_1$-$C_{12}$ (hetero)alkyl, or $C_5$-$C_{12}$ (hetero)aryl. Each $R^4$ is independently H, $C_1$-$C_{12}$ (hetero)alkyl, or $C_5$-$C_{12}$ (hetero)aryl. Group $R^5$ is hydrogen, $C_1$-$C_{12}$ (hetero)alkyl, or $C_5$-$C_{12}$ (hetero)aryl, or —N($R^4$)$_2$. The variable m is equal to 1 or 2. The term "Polymer" in Formula (I) refers to all portions of the guanidinyl-containing polymer except the x groups of formula —C($R^1$)=N—$R^2$—N($R^3$)—[C(=N$R^4$)—N$R^4$$R^5$—]$_m$. The term x is a variable equal to at least 1.

Guanidinyl-containing polymers of Formula (IV) are the reaction product of a carbonyl-containing polymer and a suitable guanylating agent for reaction with a carbonyl group. The carbonyl-containing polymer used as a precursor polymer to prepare a guanidinyl-containing polymer of Formula (IV) can be represented by the formula Polymer—C(O)—$R^1$. The carbonyl-containing polymer precursor typically has many groups —C(O)—$R^1$ but Formula (IV) shows only one for ease of discussion purposes only. The carbonyl group —C(O)—$R^1$ is an aldehyde group (when $R^1$ is hydrogen) or a ketone groups (when R1 is a (hetero)alkyl or (hetero)aryl). Although the carbonyl-group can be part of the polymeric backbone or part of a pendant group from the polymeric backbone, it is typically in a pendant group.

In some embodiments, the carbonyl-containing polymer is the polymerized product of a monomer composition that includes an ethylenically unsaturated monomer having a carbonyl group, preferably a ketone group. Suitable monomers having a carbonyl group include, but are not limited to, acrolein, vinyl methyl ketone, vinyl ethyl ketone, vinyl isobutyl ketone, isopropenyl methyl ketone, vinyl phenyl ketone, diacetone (meth)acrylamide, acetonyl acrylate, and acetoacetoxyethyl (meth)acrylate.

In other embodiments, the carbonyl-containing polymer is the polymerized product of a monomer composition that includes carbon monoxide and one or more ethylenically unsaturated monomer (i.e., the carbonyl-containing polymer is a carbon monoxide copolymers). An example of a carbon monoxide containing copolymer is ELVALOY 741, a terpolymer of ethylene/vinyl acetate/carbon monoxide from DuPont (Wilmington, Del., USA).

In addition to carbon monoxide and/or an ethylenically unsaturated monomer with a carbonyl group (e.g., a ketone group), the monomer composition used to form that carbonyl-containing polymer can optionally further comprise ethylenically unsaturated hydrophilic monomer units. As used herein, "hydrophilic monomers" are those polymerizable monomers having water miscibility (water in monomer) of at least 1 weight percent preferably at least 5 weight percent without reaching a cloud point, and contain no functional groups that would interfere with the binding of biological substances to the ligand group. The carbonyl-containing polymer may include, for example, 0 to 90 weight percent of the hydrophilic monomers in the monomer composition. If present, the hydrophilic monomer can be present in an amount in a range of 1 to 90 weight percent, 1 to 75 weight percent, 1 to 50 weight percent, 1 to 25 weight percent, or 1 to 10 weight percent based on based a total weight of the monomer composition.

The hydrophilic groups of the hydrophilic monomers may be neutral, have a positive charge, a negative charge, or a combination thereof. Hydrophilic monomers with an ionic group can be neutral or charged depending on the pH conditions. Hydrophilic monomers are typically used to impart a desired hydrophilicity (i.e. water solubility or dispersibility) to the carbonyl-containing polymer. A negatively charged hydrophilic monomer may be included as long as it is in small enough amounts that it doesn't interfere with the binding interaction of the guanidinyl group.

Some exemplary hydrophilic monomers that are capable of providing a positive charge are amino (meth)acrylates or amino (meth)acrylamides of Formula (V) or quaternary ammonium salts thereof. The counter ions of the quaternary ammonium salts are often halides, sulfates, phosphates, nitrates, and the like.

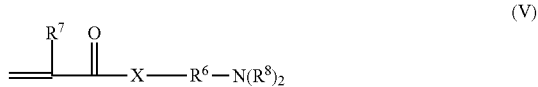

In Formula (V), the group X is oxy (i.e., —O—) or —N$R^3$— where $R^3$ is hydrogen, $C_1$-$C_{12}$ (hetero)alkyl, or $C_5$-$C_{12}$ (hetero)aryl. The group $R^6$ is a $C_2$ to $C_{10}$ alkylene, preferably a $C_2$-$C_6$ alkylene. The group $R^7$ is independently hydrogen or methyl. Each $R^8$ is independently hydrogen, alkyl, hydroxyalkyl (i.e., an alkyl substituted with a hydroxy), or aminoalkyl (i.e., an alkyl substituted with an amino). Alternatively, the two $R^8$ groups taken together with the nitrogen atom to which they are attached can form a heterocyclic group that is aromatic, partially unsaturated (i.e., unsaturated but not aromatic), or saturated, wherein the heterocyclic group can optionally be fused to a second ring that is aromatic (e.g., benzene), partially unsaturated (e.g., cyclohexene), or saturated (e.g., cyclohexane).

It will be understood with respect to Formula (V) that the depicted ethylenically unsaturated (meth)acryloyl group ($CH_2$=C($R^7$)—C(O)— group) may be replaced by another ethylenically unsaturated group of reduced reactivity, such as vinyl, vinyloxy, allyl, allyloxy, and acetylenyl.

In some embodiments of Formula (V), both $R^8$ groups are hydrogen. In other embodiments, one $R^8$ group is hydrogen and the other is an alkyl having 1 to 10, 1 to 6, or 1 to 4 carbon atoms. In still other embodiments, at least one of $R^8$ groups is a hydroxy alkyl or an amino alkyl that have 1 to 10, 1 to 6, or 1 to 4 carbon atoms with the hydroxy or amino group being positioned on any of the carbon atoms of the alkyl group. In yet other embodiments, the $R^8$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to imidazolyl. The heterocyclic group can be fused to an additional ring such as a benzene, cyclohexene, or cyclohexane. Exemplary heterocyclic groups fused to an additional ring include, but are not limited to, benzoimidazolyl.

Exemplary amino acrylates (i.e., "X" in Formula (V) is oxy) include N,N-dialkylaminoalkyl (meth)acrylates such as, for example, N,N-dimethylaminoethyl(meth)acrylate, N,N-dimethylaminoethylacrylate, N,N-diethylaminoethylacrylate, N,N-dimethylaminopropyl(meth)acrylate, N-tert-butylaminopropyl(meth)acrylate, and the like.

Exemplary amino (meth)acrylamides (i.e., "X" in Formula (V) is —$NR^3$—) include, for example, N-(3-aminopropyl)methacrylamide, N-(3-aminopropyl)acrylamide, N-[3-(dimethylamino)propyl]methacrylamide, N-[3-(dimethylamino)propyl]acrylamide, N-(3-imidazolylpropyl)methacrylamide, N-(3-imidazolylpropyl)acrylamide, N-(2-imidazolylethyl)methacrylamide, N-(1,1-dimethyl-3-imidazolylpropyl)methacrylamide, N-(1,1-dimethyl-3-imidazolylpropyl)acrylamide, N-(3-benzimidazolylpropyl)acrylamide, and N-(3-benzimidazolylpropyl)methacrylamide.

Exemplary quaternary salts of the monomers of Formula (V) include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Other monomers that can provide positively charged groups to the polymer include the dialkylaminoalkylamine adducts of alkenylazlactones (e.g., 2-(diethylamino)ethylamine, (2-amino ethyl)trimethylammonium chloride, and 3-(dimethylamino)propylamine adducts of vinyldimethylazlactone) and diallylamine monomers (e.g., diallylammonium chloride and diallyldimethylammonium chloride).

In some preferred embodiments, the optional hydrophilic monomer may have an ethylenically unsaturated group such as a (meth)acryloyl group and a poly(alkylene oxide) group. For example, the hydrophilic monomer can be a poly (alkylene oxide) mono(meth)acrylate compounds, where the terminus is a hydroxy group, or an alkyl ether group. Such monomers are of the general Formula (VI).

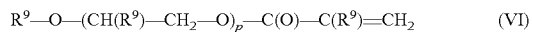

$R^9$—O—(CH($R^9$)—$CH_2$—O)$_p$—C(O)—C($R^9$)=$CH_2$     (VI)

In Formula (VI), each $R^9$ is independently hydrogen or a $C_1$-$C_4$ alkyl. The variable p is at least 2 such as, for example, 2 to 100, 2 to 50, 2 to 20, or 2 to 10.

In one embodiment, the poly(alkylene oxide) group (depicted as —(CH($R^9$)—CH2-O)$_p$—) is a poly(ethylene oxide). In another embodiment, the poly(alkylene oxide) group is a poly(ethylene oxide-co-propylene oxide). Such copolymers may be block copolymers, random copolymers, or gradient copolymers.

Other representative examples of suitable hydrophilic monomers include but are not limited to acrylic acid; methacrylic acid; 2-acrylamido-2-methyl-1-propanesulfonic acid; 2-hydroxyethyl (meth)acrylate; N-vinylpyrrolidone; N-vinylcaprolactam; acrylamide; mono- or di-N-alkyl substituted acrylamide; t-butyl acrylamide; dimethylacrylamide; N-octyl acrylamide; poly(alkoxyalkyl) (meth)acrylates including 2-(2-ethoxyethoxy)ethyl (meth)acrylate, 2-ethoxyethyl (meth)acrylate, 2-methoxyethoxyethyl (meth) acrylate, 2-methoxyethyl methacrylate, polyethylene glycol mono(meth)acrylates; alkyl vinyl ethers, including vinyl methyl ether; and mixtures thereof. Preferred hydrophilic monomers include those selected from the group consisting of dimethylacrylamide, 2-hydroxyethyl (meth)acrylate, and N-vinylpyrrolidinone.

In some embodiments, the monomer composition used to form the carbonyl-containing polymer can optionally include a hydrophobic monomer. As used herein, the term "hydrophobic monomer" refers monomers having a water miscibility (water in monomer) that is less than 1 weight percent. The hydrophobic monomers can be used in amounts that do not deleteriously affect the binding performance of the guanidinyl-containing monomer polymer and/or the water dispersibility of the guanidinyl-containing polymer. When present, the hydrophobic monomer is typically present in an amount in a range of 1 to 20 weight percent, 1 to 10 weight percent, or 1 to 5 weight percent based on a total weight of monomers in the monomer composition.

Useful classes of hydrophobic monomers include alkyl acrylate esters and amides, exemplified by straight-chain, cyclic, and branched-chain isomers of alkyl esters containing $C_1$-$C_{30}$ alkyl groups and mono- or dialkyl acrylamides containing $C_1$-$C_{30}$ alkyl groups. Useful specific examples of alkyl acrylate esters include: methyl acrylate, ethyl acrylate, n-propyl acrylate, n-butyl acrylate, iso-amyl acrylate, n-hexyl acrylate, n-heptyl acrylate, isobornyl acrylate, n-octyl acrylate, iso-octyl acrylate, 2-ethylhexyl acrylate, iso-nonyl acrylate, decyl acrylate, undecyl acrylate, dodecyl acrylate, lauryl acrylate, tridecyl acrylate, and tetradecyl acrylate. Useful specific examples of alkyl acrylamides include mono- and diacrylamides having pentyl, hexyl, heptyl, isobornyl, octyl, 2-ethylhexyl, iso-nonyl, decyl, undecyl, dodecyl, tridecyl, and tetradecyl groups may be used. The corresponding methacrylate esters may be used.

Additional useful classes of hydrophobic monomers further include vinyl monomers such as vinyl acetate, styrenes, and alkyl vinyl ethers, and maleic anhydride.

The monomer composition used to form the carbonyl-containing polymer is typically combined with a free radical initiator to form the polymerized product. Any suitable free radical initiator can be used. The initiator is typically present in an amount in the range of 0.01 to 5 weight percent, in the range of 0.01 to 2 weight percent, in the range of 0.01 to 1 weight percent, or in the range of 0.01 to 0.5 weight percent based on a total weight of monomers in the monomer composition.

In some embodiments, a thermal initiator is used. Thermal initiators can be water-soluble or water-insoluble (i.e., oil-soluble) depending on the particular polymerization method used. Suitable water-soluble initiators include, but are not limited to, persulfates such as potassium persulfate, ammonium persulfate, sodium persulfate, and mixtures thereof; an oxidation-reduction initiator such as the reaction product of a persulfate and a reducing agent such as a metabisulfite (e.g., sodium metabisulfite) or a bisulfate (e.g., sodium bisulfate); or 4,4'-azobis(4-cyanopentanoic acid) and its soluble salts (e.g., sodium or potassium). Suitable oil-soluble initiators include, but are not limited to, various azo compound such as those commercially available under the trade designation VAZO from DuPont (Wilmington, Del., USA) including VAZO 67, which is 2,2'-azobis(2-methylbutane nitrile), VAZO 64, which is 2,2'-azobis(isobutyronitrile), and VAZO 52, which is (2,2'-azobis(2,4-dimethylpentanenitrile); and various peroxides such as benzoyl peroxide, cyclohexane peroxide, lauroyl peroxide, and mixtures thereof.

In many embodiments, a photoinitiator is used. Some exemplary photoinitiators are benzoin ethers (e.g., benzoin methyl ether or benzoin isopropyl ether) or substituted benzoin ethers (e.g., anisoin methyl ether). Other exemplary photoinitiators are substituted acetophenones such as 2,2-diethoxyacetophenone or 2,2-dimethoxy-2-phenylacetophenone (commercially available under the trade designation IRGACURE 651 from BASF Corp. (Florham Park, N.J., USA) or under the trade designation ESACURE KB-1 from Sartomer (Exton, Pa., USA)). Still other exemplary photoinitiators are substituted alpha-ketols such as 2-methyl-2-hydroxypropiophenone, aromatic sulfonyl chlorides such as 2-naphthalenesulfonyl chloride, and photoactive oximes such as 1-phenyl-1,2-propanedione-2-(O-ethoxycarbonyl) oxime. Other suitable photoinitiators include, for example, 1-hydroxycyclohexyl phenyl ketone (IRGACURE 184), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The guanidinyl-containing polymers according to Formula (IV) are often the reaction product of a carbonyl-containing polymer precursor and a guanylating agent of Formula (VII).

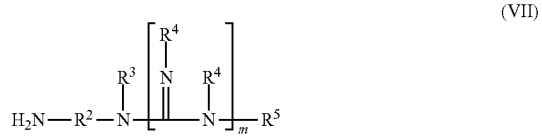

(VII)

In Formula (VII), the group $R^2$ is a covalent bond, $C_2$-$C_{12}$ (hetero)alkylene, or $C_5$-$C_{12}$ (hetero)arylene. Group $R^3$ is hydrogen, $C_1$-$C_{12}$ (hetero)alkyl, or $C_5$-$C_{12}$ (hetero)aryl. Each $R^4$ is independently hydrogen, $C_1$-$C_{12}$ (hetero)alkyl, or $C_5$-$C_{12}$ (hetero)aryl. Group $R^5$ is H, $C_1$-$C_{12}$ (hetero)alkyl, or $C_5$-$C_{12}$ (hetero)aryl, or —N($R^4$)$_2$. The variable m is equal to 1 or 2.

For ease of description, the carbonyl-containing polymer can be represented by the formula Polymer —C(=O)—$R^1$. The carbonyl group can be in the backbone or in a pendant group but is usually in a pendant group. When reacted with a guanylating agent of Formula (VII), the carbonyl group in the carbonyl-containing polymer undergoes a condensation reaction with a terminal amine group of the guanylating agent. The guanidinyl-containing polymer typically has guanidinyl-containing pendant groups of Formula (VIII).

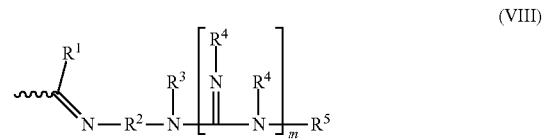

(VIII)

The groups $R^2$, $R^3$, $R^4$, and $R^5$ are the same as described above for Formula (VII). The group of formula

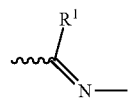

in Formula (VIII) is the linkage formed between the terminal amine of the ligand compound of Formula (VII) and the carbonyl group of the carbonyl-containing polymer. The wavy line denotes the attachment site of the group via a covalent bond to the rest of the polymer. Group $R^1$ is hydrogen (when the carbonyl group is an aldehyde group), $C_1$-$C_{12}$ (hetero)alkyl (when the carbonyl group is a ketone group and the ketone group is part of a pendant group), or $C_5$-$C_{12}$ (hetero)aryl (when the carbonyl group is a ketone group and the ketone group is part of a pendant group), or a residue of the polymer chain (when the carbonyl group is a group in the backone of the carbonyl-containing polymer). In most embodiments, the group of Formula (VIII) is part of a pendant group of the guanidinyl-containing polymer.

In other embodiments, the guanidyl-containing polymer may be prepared in which the imine linking group (~~C($R^1$)=N—) is reduced to an amine linking group (~~C($R^1$)—NH—). This may be effected by treating the extant ligand functional polymer with a reducing agent, such as sodium cyanoborohydride, or the reduction may be effected in situ by adding the reducing agent to the reaction mixture of the carbonyl functional (co)polymer and the compound of Formula V.

In many embodiments, some but not all of the carbonyl groups of the carbonyl-containing polymer are reacted with the guanylating agent of Formula (VII). Typically, at least 0.1 mole percent, at least 0.5 mole percent, at least 1 mole percent, at least 2 mole percent, at least 10 mole percent, at least 20 mole percent, or at least 50 mole percent of the carbonyl groups in the carbonyl-containing polymer precursor are reacted with the guanylating agent. Up to 100 mole percent, up to 90 mole percent, up to 80 mole percent, or up to 60 mole percent of the carbonyl groups can be reacted with the guanylating agent. For example, the guanylating agent can be used in amounts sufficient to functionalize 0.1 to 100 mole percent, 0.5 to 100 mole percent, 1 to 90 mole percent, 1 to 80 mole percent, 1 to 60 mole percent, 2 to 50 mole percent, 2 to 25 mole percent, or 2 to 10 mole percent of the carbonyl groups in the carbonyl-containing polymer.

The guanidinyl-containing polymer can be crosslinked. In some embodiments, the carbonyl-containing polymer is crosslinked prior to reaction with the guanylating agent. The carbonyl-containing polymer can be crosslinked either by addition of a crosslinking monomer in the monomer composition used to form the carbonyl-containing polymer or by reaction of some of the carbonyl groups of the previously formed carbonyl-containing polymer with a suitable crosslinking agent. In other embodiments, crosslinking can occur after reaction of the carbonyl-containing polymer with the guanylating agent. In this embodiment, crosslinking can occur by reaction of some of the remaining carbonyl groups (those carbonyl groups in the carbonyl-containing polymer precursor that were not reacted in the process of forming the guanidinyl-containing polymer) with a suitable crosslinking agent or by reaction of some of the guanidinyl groups with a crosslinking agent.

Suitable crosslinking monomers for use in the monomer composition to form the carbonyl-containing polymer include, but are not limited to, N,N'-(hetero)alkylenebis (meth)acrylamide. These crosslinking monomers have at least two (meth)acryloyl groups that can react to crosslink one polymeric chain with another polymeric chain or that can react to crosslink one part of a polymeric chain with another part of the same polymeric chain. Suitable N,N'-alkylenebis(meth)acrylamide crosslinking monomers include, but are not limited to, those having an alkylene group with 1 to 10, 1 to 8, 1 to 6, or 1 to 4 carbon atoms such as N,N'-methylenebisacrylamide, N,N'-methylenebismethacrylamide, N,N'-ethylenebisacrylamide, N,N'-ethylenebismethacrylamide, N,N'-propylenebisacrylamide, N,N'-propylenebismethacrylamide, N,N'-hexamethylenebisacrylamide, and N,N'-hexamethylenebismethacrylamide. Suitable N,N'-heteroalkylenebis(meth)acrylamide crosslinking monomers include, but are not limited to, N,N'-cystaminebisacrylamide, N,N'-piperazinebisacrylamide, and N,N'-piperazinebismethacrylamide. These crosslinking monomers are commercially available from various suppliers such as Sigma-Aldrich (Milwaukee, Wis.) and Polysciences, Inc. (Warrington, Pa.). Alternatively, these crosslinking monomers can be synthesized by procedures described in the art such as, for example, in Rasmussen, et al., *Reactive Polymers,* 16, 199-212 (1991/1992).

Suitable crosslinkers for reaction with carbonyl groups of the carbonyl-containing polymer precursor or remaining carbonyl groups of the guanidinyl-containing polymer include molecules comprising two or more amine, hydrazine, hydrazide, or O-substituted hydroxylamine moieties. Specific examples of polyamine (compounds with two or more amine groups) crosslinkers include 1,2-ethanediamine, 1,2-propanediamine, 1,3-propanediamine, 1,6-hexanediamine, tris-(2-aminoethyl)amine, diethylenetriamine, triethylenetetraamine, tetraethylenepentaamine, N,N'-bis(3-aminopropyl)piperazine, N-(2-aminoethyl)piperazine, polyethyleneimine, polyallylamine, and the like. Specific examples of polyhydrazines (compounds with two or more hydrazine groups) include 1,1'-ethylenebishydrazine, 1,1'-propylenebishydrazine, 1,1'-ethylenebis (1-cyclohexylhydrazine), 1,1'-decamethylenebis (1-n-butylhydrazine), and the like. Specific examples of useful polyhydrazides (compounds with two or more hydrazide groups) include succinic dihydrazide, adipic dihydrazide, terephthalic dihydrazide, 1,3-diaminoguanidine, and the like. Specific examples of polyhydroxylamines (compounds with two or more O-substituted hydroxylamine groups) include O,O'-ethylenebishydroxylamine(1,2-bisaminoxyethane), 1,6-bisaminoxyhexane, and the like. Alternatively, crosslinkers comprising two or more different moieties selected from amine, hydrazine, hydrazide, or O-substituted hydroxylamine moieties can be used.

Suitable crosslinkers for reaction with the guanidinyl groups of the guanidinyl-containing polymer include amine-reactive compounds such as bis- and polyaldehydes such as glutaraldehyde, bis- and polyepoxides such as butanedioldiglycidylether and ethyleneglycoldiglycidylether, polycarboxylic acids and their derivatives (e.g., acid chlorides), polyisocyanates, formaldehyde-based crosslinkers such as hydroxymethyl and alkoxymethyl functional crosslinkers, such as those derived from urea or melamine.

Rather than reacting a precursor polymer with a guanylating agent to prepare a guanidinyl-containing polymer, the guanidinyl-containing polymer can be prepared by free radical polymerization of a guanidinyl-containing monomer, which refers to a monomer having an ethylenically unsaturated group and a guanidinyl-containing group. Example guanidinyl-containing monomers are of Formula (IX) and (X).

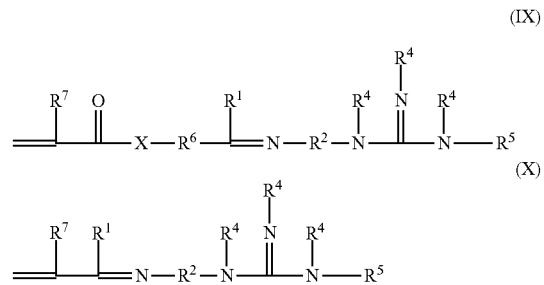

In Formulas (IX) and (X), group $R^1$ is hydrogen, $C_1$-$C_{12}$ alkyl, or $C_5$-$C_{12}$ (hetero)aryl. Group $R^2$ is a covalent bond, a $C_2$ to $C_{12}$ alkylene, a $C_5$-$C_{12}$ (hetero)arylene, a divalent group of formula

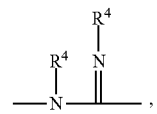

or a divalent group of formula

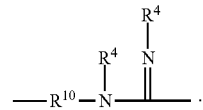

Group $R^{10}$ is $C_2$ to $C_{12}$ alkylene, or $C_5$-$C_{12}$ (hetero)arylene. Each $R^3$ is independently hydrogen, hydroxyl, $C_1$-$C_{12}$ alkyl, or $C_5$-$C_{12}$ (hetero)aryl. $R^3$ is preferably hydrogen or $C_1$-$C_4$ alkyl. Group $R^4$ is hydrogen, $C_1$-$C_{12}$ alkyl, $C_5$-$C_{12}$ (hetero) aryl, or —N($R^3$)$_2$. Preferably, $R^4$ is hydrogen or $C_1$-$C_4$ alkyl. Group X is oxy or —NR$^3$—. Group $R^6$ is a $C_2$ to $C_{12}$ alkylene. Group $R^7$ is hydrogen or CH$_3$.

The monomers of Formula (IX) and (X) can be formed, for example, by a condensation reaction of a carbonyl-containing monomer with the guanylating agent of Formula (VII). Example carbonyl-containing monomers include, but are not limited to, acrolein, vinyl methyl ketone, vinyl ethyl ketone, vinyl isobutyl ketone, isopropenyl methyl ketone, vinyl phenyl ketone, diacetone (meth)acrylamide, acetonyl acrylate, and acetoacetoxyethyl (meth)acrylate.

The monomers of Formula (IX) or (X) may be reacted to form homopolymers or can be copolymerized with other ethylenically unsaturated monomers such as any of the hydrophilic monomers described above. A free radical initiator such as those described above in the preparation of the carbonyl-containing polymer can be used. This reaction is further described in International Patent Publication WO 2011/103106 A1 (Rasmussen et al.).

Guanidinyl-containing polymers formed from a monomer of Formula (X) or (XI) are typically crosslinked by addition of a crosslinking monomer to the monomer composition. Suitable crosslinking monomers include N,N'-alkylenebis (meth)acrylamide, N,N'-heteroalkylenebis(meth)acrylamide, or a combination thereof. More specific crosslinkers are the same as described above for use in a monomer composition for preparation of the carbonyl-containing polymers. Alternatively, the guanidinyl-containing polymers can be formed without a crosslinking monomer and the guanidinyl groups can be reacted with crosslinkers as described above.

Wipes are provided that contain a substrate and a cationic coating disposed on a surface of the substrate, distributed throughout at least a portion of the substrate, or both. The substrate is typically porous and includes a sponge, nonwoven fabric, or woven fabric. The cationic coating includes the guanidinyl-containing polymer that is bound to the substrate. The guanidinyl-containing polymer can be bound to the substrate using any suitable method or means. In some embodiments, the guanidinyl-containing polymer is grafted (i.e., covalently attached) to the substrate. In other embodiments, the guanidinyl-containing polymer is contacted with the substrate prior to crosslinking and is crosslinked in the presence of the substrate. When the substrate includes fibers (e.g., the substrate includes a woven or nonwoven fabric), the crosslinked guanidinyl-containing polymer can surround fibers. The fibers and the crosslinked guanidinyl-containing polymers can be so intermingled that separation is not possible by a technique such as peeling or dissolution or by any other technique without the destruction of the wipe.

The substrate may be in any suitable form for a wipe. Some suitable substrates are woven or non-woven fabrics that are in the form of a sheet. The sheet can have any desired size and shape. Other suitable substrates are sponges that can have any desired size or shape. The substrates are usually porous. Suitable substrates are typically flexible so that the wipe can easily conform and contact various surfaces such as those that are not flat.

The substrate may be formed from any suitable thermoplastic or thermoset material. The material may be an organic polymeric material. Suitable organic polymeric materials include, but are not limited to, poly(meth)acrylates, poly(meth)acrylamides, polyolefins, poly(isoprenes), poly(butadienes), fluorinated polymers, chlorinated polymers, polyamides, polyimides, polyethers, poly(ether sulfones), poly(sulfones), poly(vinyl acetates), copolymers of vinyl acetate, such as poly(ethylene)-co-poly(vinyl alcohol), poly(phosphazenes), poly(vinyl esters), poly(vinyl ethers), poly(vinyl alcohols), poly(carbonates), polyurethanes, and cellulosic materials.

Suitable polyolefins include, but are not limited to, poly (ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoro ethylene).

Suitable polyamides include, but are not limited to, poly (iminoadipoyliminohexamethylene), poly(iminoadipoylimi-nodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

Suitable cellulosic materials include cotton, rayon, and blends thereof.

In some embodiments, the substrate is formed from propylene polymers (e.g., homopolymer or copolymers). Polypropylene polymers, particularly polypropylene homopolymers, can be desirable for some applications due to properties such as non-toxicity, inertness, low cost, and the ease with which it can be extruded, molded, and formed into articles. Polypropylene polymers can be formed, for example, into porous sheets of woven or nonwoven fibers.

Some substrates are nonwoven fabrics. As used herein, the term "nonwoven fabric" refers to a fabric or web that has a structure of individual fibers or filaments that are randomly and/or unidirectionally interlaid in a mat-like fashion. The individual fibers or threads are not interlaid in an identifiable pattern as in a knitted or woven fabric. Examples of suitable nonwoven fabrics include, but are not limited to, melt-blown fabrics, spun-bond fabrics, carded fabrics, wetlaid fabrics, and air-laid fabrics.

Spun-bonded fibers are typically small diameter fibers that are formed by extruding molten thermoplastic polymer as filaments from a plurality of fine, usually circular capillaries of a spinneret with the diameter of the extruded fibers being rapidly reduced. Melt-blown fibers are typically formed by extruding the molten thermoplastic material through a plurality of fine, usually circular, die capillaries as molten threads or filaments into a high velocity, usually heated gas (e.g., air) stream which attenuates the filaments of molten thermoplastic material to reduce their diameter. Thereafter, the melt-blown fibers are carried by the high velocity gas stream and are deposited on a collecting surface to from a fabric of randomly disbursed melt-blown fibers. Any of the non-woven fabrics may be made from a single type of fiber or two or more fibers that differ in the type of thermoplastic polymer and/or thickness.

Wet-laid fibers can be formed into sheets by forming a slurry that contains a) fibers and b) a suspending liquid such as water, a water-miscible organic solvent, or a mixture thereof. The slurry is placed in mold or deposited in a layer. The suspending liquid is removed to form a sheet or mat. The sheet or mat is then dried. In some embodiments, a polymeric binder is included in the dispersion. In other embodiments, a polymeric binder can be applied after formation of a sheet or mat. The polymeric binder is often a latex polymer.

Further details on the manufacturing method of nonwoven fabrics may be found in Wente, Superfine Thermoplastic Fibers, 48 INDUS. ENG. CHEM. 1342(1956), or in Wente et al., Manufacture Of Superfine Organic Fibers, (Naval Research Laboratories Report No. 4364, 1954).

The cationic coating composition that includes the guanidinyl-containing polymer is applied to the substrate. Coating methods include the techniques commonly known such as dip, spray, knife, bar, slot, slide, die, roll, and gravure coating. The cationic coating can be disposed on a surface of the substrate or distributed throughout the substrate. For example, the cationic coating composition can be applied to the surface of the substrate. Depending on the porosity of the substrate, the viscosity of the cationic coating composition, and the relative volume of the cationic coating composition to that of the substrate, at least some of the cationic coating composition can permeate into the substrate. In some examples, the cationic coating can be poured over the substrate such that the substrate is immersed in or covered with the cationic coating composition. The cationic coating composition often includes a liquid such as water, an organic solvent such as a polar organic solvent (e.g., a polar that is miscible with water), or a mixture thereof. The cationic coating composition can additionally include the crosslinking agent for the guanidinyl-containing polymer. Depending on the chemistry used to bind the gaunidinyl-containing polymer to the substrate, a compound for grafting or attaching the guanidinyl-containing polymer to the substrate can be included in the cationic coating composition. After application to the substrate, the cationic coating composition can be dried to remove the liquid or any desired portion of the liquid. In some embodiments, the drying to remove the liquid is accomplished through evaporation.

In some embodiments, the cationic coating composition is applied to the substrate by first applying the precursor polymer for the guanidinyl-containing polymer followed by application of the guanylating agent. For example, an amino-containing polymer precursor or a carbonyl-containing polymer precursor can be applied to the substrate in a first coating composition. A second coating composition can then be applied that includes the guanylating agent. The crosslinking agent can be added in the first coating composition with the precursor polymer, in the second coating composition with the guanylating agent, or in a third coating composition. Any of the coating compositions can include an optional compound for grafting the guanidinyl-containing polymer to the substrate.

In other embodiments, the guanidinyl-containing polymer is applied to the substrate. The coating composition that contains the guanidinyl-containing polymer can further include a crosslinking agent, an optional grafting compound, or a mixture thereof. Alternatively, the crosslinking agent and/or optional grafting agent can be added in a second coating composition.

Some substrates have amine-reactive functional groups such as halide groups, epoxy groups, ester groups, or isocyanate groups. These amine-reactive groups can react with amino groups of the guanidinyl-containing polymer. The amino groups can be part of the guanidinyl group (such as a terminal amino group) or any other amino groups that are present in the guanidinyl-containing polymer. For example, if the guanidinyl-containing polymer was formed from an amino-containing polymer precursor, there can be amino groups in the backbone of the guanidinyl-containing polymer.

The amine-reactive functional groups on the substrate may be part of the polymeric material used to form the substrate or may be provided by any of the techniques known to one in the art. In one embodiment, the substrate may have a primer layer containing a polymer having amine-reactive functional groups. That is, the substrate includes a base polymer layer and a primer layer. Especially useful polymers of use in the primer layer are azlactone functional polymers such as those described in U.S. Pat. No. 7,101,621 (Haddad et al.). Such primer layer coatings are typically hydrophilic and are compatible with the cationic coating composition. Useful coating techniques for the primer layer include applying a solution or dispersion of the polymer having amine-reactive functional groups, optionally further including a crosslinker, onto the substrate.

Coating methods include the techniques commonly known such as dip, spray, knife, bar, slot, slide, die, roll, and gravure coating. The application step is generally followed by evaporating the solvent to form the polymer coating.

In some embodiments, the polymer having amine-reactive functional groups may be grafted to the surface of a substrate by ionizing radiation-initiated graft polymerization of a monomer having a free-radically polymerizable group and a second functional group reactive with the guanidinyl-containing polymer. One such polymer having an amine-reactive functional group is described U.S. Patent Application Publication No. 2010/0075560 (Seshadri et al.). Suitable monomers include, for example, an azlactone-functional monomer, isocyanatoethyl (meth)acrylate, and a glycidyl (meth)acrylate. Other suitable monomers include, for example, those having a carbonyl group as described in U.S. Pat. No. 8,377,672 (Rasmussen et al.). The monomers can graft (i.e., form a covalent bond) to the surface of the substrate when exposed to an ionizing radiation, preferably e-beam or gamma radiation. That is, reaction of an ethylenically unsaturated group (e.g., a (meth)acryloyl group) of the monomer with the surface of the substrate in the presence of the ionizing radiation results in grafting to the substrate via the ethylenically unsaturated group.

Some substrates have carbonyl-reactive groups such as amines. These carbonyl-reactive groups can react with a carbonyl-containing polymer precursor prior to reaction with the guanylating agent or can react with any residual carbonyl groups in the guanidinyl-containing polymer after reaction with the guanylating agent.

The carbonyl-reactive functional groups on the substrate may be part of the polymeric material used to form the substrate or may be provided by any of the techniques known to one in the art. In some embodiments, the carbonyl-reactive groups can be grafted to the surface of a substrate by ionizing radiation-initiated graft polymerization of a monomer having a free-radically polymerizable group and a second group capable of reacting with a carbonyl group of either the carbonyl-containing precursor or any residual carbonyl groups in the guanidinyl-containing polymer after reaction with a guanylating agent. Such monomers are various amino-containing monomers such as those of Formula (V) where $R^8$ is hydrogen.

In another method of bonding the guanidinyl-containing polymer to the substrate, a compound such as benzophenone or acetophenone can be added to the monomer composition used to form the carbonyl-containing precursor. Upon exposure to UV radiation, the benzophenone or acetophenone can abstract a hydrogen atom from the polymeric material of the substrate. This abstraction results in the formation of a free radical site on the polymeric material of the substrate. The monomers then interact with the free radical site and become graft polymerized onto the substrate. The covalently attached carbonyl-containing polymer can then be treated with a guanylating agent to form the guanidinyl-containing polymer.

The bonding of the guanidinyl-containing polymer to the substrate provides enhanced affinity for various microorganisms while retaining many of the desirable features of the substrate such as mechanical stability, thermal stability, porosity, and flexibility. The wipes typically contain an amount of the bound guanidinyl-containing polymer in a range of 0.1 to 10 weight percent, in a range of 0.1 weight percent to 50 weight percent, in a range of 0.1 to 3 weight percent, in a range of 0.1 to 2, or in a range of 0.1 weight percent to 1 weight percent, based on a total weight of the wipe.

A method of removing microorganisms from a microorganism-contaminated surface is provided. The method includes preparing a wipe that includes (a) a substrate comprising a sponge, a woven fabric, or nonwoven fabric and (b) a cationic coating disposed on a surface of the substrate, distributed throughout at least a portion of the substrate, or both. The cationic coating includes a guanidinyl-containing polymer that is crosslinked, that is covalently attached to the substrate, or both. The method further includes contacting the wipe in the presence of a liquid with an area of the microorganism-contaminated surface, wherein at least 99 percent of microorganisms present in the area are removed from the microorganism-contaminated surface.

The wipes are suitable for the removal of microorganisms, especially spores, from a microorganism-contaminated surface. Bacterial spores are known to be adherent and difficult to remove from a variety of surfaces, as well as being resistant to most antimicrobial treatments. Because the guanidinyl-containing polymer can interact with microorganisms, the wipe can remove the microorganisms from a surface and prevent their transfer to another surface. The removal of the microorganisms is believed to be, at least in part, due to an ionic interaction. The guanidinyl group of the guanidinyl-containing polymer is typically positively charged over nearly the entire pH range available in aqueous media, and will bind negatively charged or near neutral species. All cells, including microorganisms, are negatively charged due to the presence of groups, such as carboxylates, sulfates, or phosphates, on their surfaces. Positively charged species are likely not to bind.

The wipe can be used for the removal of various microorganisms including, for example, bacteria (gram-positive bacteria and gram-negative bacteria), fungi, yeasts, protozoans, viruses (enveloped viruses and non-enveloped viruses (norovirus, poliovirus, hepatitis A virus, rhinovirus, and combinations thereof)), bacterial spores (for example, endospore forms of *Bacillus* and *Clostridium* microorganisms), and the like, and combinations thereof.

Genera of microorganisms to be removed include, but are not limited to, *Listeria, Escherichia, Salmonella, Campylobacter, Clostridium, Helicobacter, Mycobacterium, Staphylococcus, Shigella, Enterococcus, Bacillus, Neisseria, Shigella, Streptococcus, Vibrio, Yersinia, Bordetella, Borrelia, Pseudomonas, Saccharomyces, Candida,* and the like, and combinations thereof.

Specific microorganism strains that can be targets for detection include *Escherichia coli, Yersinia enterocolitica, Yersinia pseudotuberculosis, Vibrio cholerae, Vibrio parahaemolyticus, Vibrio vulnificus, Listeria monocytogenes, Staphylococcus aureus, Salmonella enterica, Saccharomyces cerevisiae, Candida albicans, Staphylococcal enterotoxin* ssp, *Bacillus cereus, Bacillus anthracia, Bacillus atrophaeus, Bacillus subtilis, Clostridium perfringens, Clostridium botulinum, Clostridium difficile, Clostridium sporogenes, Enterobacter sakazakii, Pseudomonas aeruginosa,* and the like, and combinations thereof.

Microorganisms (including spore forms) that have been captured or bound (for example, by adsorption) by the wipe can be detected by essentially any desired method that is currently known or hereafter developed. Such methods include, for example, culture-based methods (which can be preferred when time permits), microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism capture optionally can include washing to remove sample matrix components.

Suitable culture-based methods of detecting microorganisms can include the use of a thin film culture plate device (e.g., an Aerobic Count PETRIFILM culture plate device, commercially available from 3M Co., St. Paul, Minn., or the thin film culture plate devices described in U.S. Pat. No. 4,565,783 (Hansen et al.), U.S. Pat. No. 5,089,413 (Hansen et al.), and U.S. Pat. No. 5,232,838 (Crandall et al.)).

Immunological detection is detection of an antigenic material derived from a target organism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process.

Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification), which is often a preferred method. The captured or bound microorganisms can be lysed to render their genetic material available for assay. Lysis methods are well-known and include, for example, treatments such as sonication, osmotic shock, high temperature treatment (for example, from about 50° C. to about 100° C.), and incubation with an enzyme such as lysozyme, glucolase, zymolase, lyticase, proteinase K, proteinase E, and viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adensosine triphosphate (ATP) detection methods including those described in U.S. Pat. No. 7,422,868 (Fan et al.).

When the wipe is contacted in the presence of a liquid with an area of a microorganism-contaminated surface, at least 99 percent of the microorganisms are removed from the area contacted with the wipe. In some embodiments, at least 99.1 percent, at least 99.2 percent, at least 99.3 percent, at least 99.4 percent, at least 99.5 percent, at least 99.6 percent, at least 99.7 percent, at least 99.8 percent, or even at least 99.9 percent of the microorganisms are removed from the area contacted with the wipe.

Liquid is typically present in the area of the microorganism-contaminated surface that is contacted with the wipe. The liquid can be present on the wipe, on the microorganism-contaminated surface, or both. The liquid is typically water, a water-miscible organic solvent, or a mixture thereof. Suitable water-miscible organic solvents are often alcohols such as those having 1 to 4 carbon atoms (e.g., methanol, ethanol, isopropanol). In many embodiments, the liquid is water or a mixture of water and the water-miscible organic solvent. The liquid typically contains at least 10 weight percent, at least 20 weight percent, or at least 50 weight percent water based on a total weight of the liquid. The amount of water can be up to 100 weight percent, up to 90 weight percent, up to 80 weight percent, or up to 60 weight percent of the liquid.

The liquid can include other ingredients suitable for removal of microorganisms from a microorganism-contaminated surface such as, for example, a disinfectant or other suitable cleaning aids, including those commonly used on hard surfaces. These other ingredients are typically soluble in water and/or a water-miscible organic solvent. Examples of suitable disinfectants can include, but are not limited to, lower alcohols, oxidizing agents (e.g., hydrogen peroxide, peracetic acid, sodium hypochlorite, and the like), phenolics, quaternary ammonium compounds, antimicrobial biguanides, and antimicrobial metals.

In some embodiments, the wipe is provided in a wet form. That is the wipe includes a liquid. The amount of liquid can be up to 10 times, 9 times, 8 times, 7 times, 6 times, 5 times, 4.5 times, 4 times, 3.5 times, 3 times, 2 times or even up to 1 times of the weight of the dry wipe, (i.e., the weight of the wipe without the liquid, which corresponds to the weight of the substrate plus the weight of the cationic coating). In some embodiments, the wet wipe is at least 0.1 times, 0.2 times, 0.3 times. 0.4 times, or even at least 0.5 times of the weight of the dry wipe.

The wipes are useful, for example, for removing microorganisms from a microorganism-contaminated surface, or for wiping surfaces suspected of being contaminated. For example, the wipes are useful for wiping surfaces (e.g., solid surfaces) in a hospital room, surfaces in a food preparation or serving area, and surfaces frequently touched such as door knobs, handrails, and the like.

The binding of microorganisms to the coated wipes is preferably essentially irreversible in order to minimize transfer of the microorganisms to another surface or to the same surface after cleaning. In some embodiments, when the wipe is brought in contact with a second surface or brought in contact with the previously cleaned surface after being in contact with a microorganism-contaminated surface, the wipe transfers no more than 0.2 percent, no more than 0.1 percent, no more than 0.09 percent, no more than 0.08 percent, no more than 0.07 percent, no more than 0.06 percent, no more than 0.05 percent, no more than 0.04 percent, no more than 0.03 percent, no more than 0.02 percent, or even no more than 0.01 percent, of the number of microorganisms removed from a microorganism-contaminated surface to the other surface.

The high removal of microorganisms from a microorganism-contaminated surface and the low transfer of microorganisms to another surface or to the same surface after cleaning is believed to be a unique characteristic of the guanidinyl group of the guanidinyl-containing polymer coating. In addition to the ionic interaction between the positively charged guanidinyl group and the negatively charged microorganisms, the guanidinyl group is capable of additional types of interaction, including hydrogen bonding and hydrophobic interaction types of binding. These additional types of interaction may increase the strength of the binding interaction between the coated wipe and the microorganism and, in some instances, make it essentially irreversible. This binding interaction is often maintained under a variety of conditions, such as over wide pH ranges, under high ionic strength conditions, and in the presence of other additives, such as surfactants.

The low transfer is also facilitated by the crosslinking of the guanidinyl-containing polymer and/or the binding of the cationic coating (e.g., binding of the guanidinyl-containing polymer) to the substrate. The crosslinked or grafted guanidinyl-containing polymer is typically not soluble in the liquid used with the wipe which results in minimal residue being left behind on a surface after being cleaned with the wipe. The binding of the cationic coating to the substrate further increases the likelihood that the removed microorganisms will not be transferred to another surface but will remain on the wipe.

In many embodiments, the wipes are disposable after use.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Various embodiments are provided that include a wipe and a method of using the wipe to remove microorganisms.

Embodiment 1 is a wipe that includes (a) a substrate comprising a sponge, a woven fabric, or nonwoven fabric and (b) a cationic coating disposed on a surface of the substrate, distributed throughout at least a portion of the substrate, or both. The cationic coating contains a guanidinyl-containing polymer that is crosslinked, covalently bonded to the substrate, or both. When the wipe is contacted in the presence of a liquid with an area of a microorganism-contaminated surface, at least 99 percent of microorganisms present on the microorganism-contaminated surface are removed from the area by the wipe, and when the wipe is contacted in the presence of the liquid with the area of the microorganism-contaminated surface and then contacted with a second surface, no more than 0.2 percent of the microorganisms are transferred from the wipe to the second surface.

Embodiment 2 is the wipe of embodiment 1, wherein the guanidinyl-containing polymer is a reaction product of (a) a guanylating agent and (b) a carbonyl-containing polymer precursor or an amino-containing polymer precursor.

Embodiment 3 is the wipe of one of embodiment 1 or 2, wherein the guanidinyl-containing polymer is of the Formula (I):

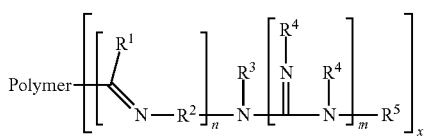

(I)

wherein R¹ is hydrogen, $C_1$-$C_{12}$ (hetero)alkyl, a $C_5$-$C_{12}$ (hetero)aryl, or a residue of the polymer chain; R² is a covalent bond, a $C_2$ to $C_{12}$ (hetero)alkylene, or a $C_5$-$C_{12}$ (hetero)arylene; R³ is hydrogen, $C_1$-$C_{12}$ (hetero)alkyl, $C_5$-$C_{12}$ (hetero)aryl, or a residue of the polymer chain when n is 0; each R⁴ is independently hydrogen, $C_1$-$C_{12}$ (hetero)alkyl, $C_5$-$C_{12}$ (hetero)aryl; R⁵ is hydrogen, $C_1$-$C_{12}$ (hetero)alkyl, or $C_5$-$C_{12}$ (hetero)aryl, or —N(R⁴)₂; n is 0 or 1; m is 1 or 2; and x is an integer equal to at least 1.

Embodiment 4 is the wipe of embodiment 3, wherein the guanidinyl-containing polymer is of Formula (II).

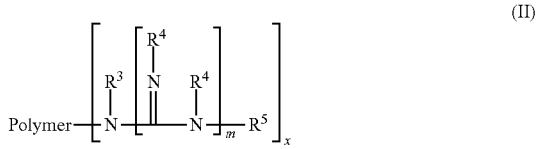

(II)

Embodiment 5 is the wipe of embodiment 3, wherein the guanidinyl-containing polymer is of Formula (IV).

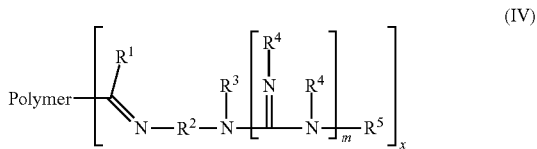

(IV)

Embodiment 6 is the wipe of any one of embodiments 1 to 3 or 5, wherein the guanidinyl-containing polymer is a reaction product of (a) a guanylating agent and (b) a carbonyl-containing polymer precursor, and wherein 1 to 90 mole percent of the carbonyl groups of the carbonyl-containing polymer precursor are reacted with the guanylating agent.

Embodiment 7 is the wipe of any one of embodiments 1 to 3 or 5, wherein the guanidinyl-containing polymer is a reaction product of (a) a guanylating agent and (b) a carbonyl-containing polymer precursor, and wherein the guanidinyl-containing polymer is crosslinked with a N,N'-(hetero)alkylenebis(meth)acrylamide.

Embodiment 8 is the wipe of any one of embodiments 1 to 4, wherein the guindidinyl-containing polymer is a reaction product of a (a) guanylating agent and (b) an amino-containing polymer precursor, and wherein 1 to 90 mole percent of the amino groups of the amino-containing polymer precursor are reacted with the guanylating agent.

Embodiment 9 is the wipe of any one of embodiments 1 to 4 wherein the guanidinyl-containing polymer is a reaction product of (a) a guanylating agent and (b) an amino-containing polymer, and wherein the guanidinyl-containing polymer is crosslinked with a polyglycidylether.

Embodiment 10 is the wipe of any one of embodiments 1 to 9, wherein the guanidinyl-containing polymer is present in an amount of 0.1 weight percent to 10 weight percent based on a total weight of the wipe.

Embodiment 11 is the wipe according to any one of embodiments 1 to 10, wherein the liquid comprises water, a water-miscible organic solvent, or a mixture thereof.

Embodiment 12 is the wipe according to any one of embodiments 1 to 11, wherein the substrate is a woven fabric or nonwoven fabric comprising fibers and wherein the crosslinked guanidinyl-containing polymer surrounds at least some of the fibers.

Embodiment 13 is the wipe according to any one of embodiments 1 to 12, wherein the guanidinyl-containing polymer is covalently attached directly to the substrate.

Embodiment 14 is the wipe according to any one of embodiments 1 to 13, wherein the substrate further comprises a base polymer layer and a primer layer and wherein the cationic coating is covalently attached to the primer layer.

Embodiment 15 is a method of removing microorganisms from a microorganism-contaminated surface. The method includes preparing a wipe that includes (a) a substrate comprising a sponge, a woven fabric, or nonwoven fabric and (b) a cationic coating disposed on a surface of the substrate, distributed throughout at least a portion of the substrate, or both. The cationic coating contains a guanidinyl-containing polymer that is crosslinked and that is bound to the substrate. The method further includes contacting the wipe in the presence of a liquid with an area of the microorganism-contaminated surface, wherein at least 99 percent of microorganisms present on the microorganism-contaminated surface are removed from the area by the wipe.

Embodiment 16 is the method of embodiment 15, wherein the guanidinyl-containing polymer is a reaction product of (a) a guanylating agent and (b) a carbonyl-containing polymer precursor or an amino-containing polymer precursor.

Embodiment 17 is the method of embodiment 15 or 16, wherein the guanidinyl-containing polymer is of the Formula (I):

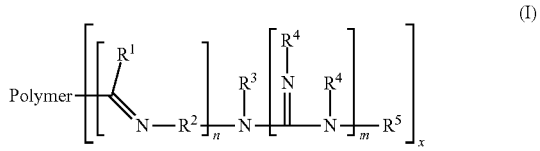

(I)

wherein R¹ is hydrogen, $C_1$-$C_{12}$ (hetero)alkyl, a $C_5$-$C_{12}$ (hetero)aryl, or a residue of the polymer chain; R² is a covalent bond, a $C_2$ to $C_{12}$ (hetero)alkylene, or a $C_5$-$C_{12}$ (hetero)arylene; R³ is hydrogen, $C_1$-$C_{12}$ (hetero)alkyl, $C_5$-$C_{12}$ (hetero)aryl, or a residue of the polymer chain when n is 0; each R⁴ is independently hydrogen, $C_1$-$C_{12}$ (hetero)alkyl, $C_5$-$C_{12}$ (hetero)aryl; R⁵ is hydrogen, $C_1$-$C_{12}$ (hetero)alkyl, or $C_5$-$C_{12}$ (hetero)aryl, or —N(R⁴)₂; n is 0 or 1; m is 1 or 2; and x is an integer equal to at least 1.

EXAMPLES

Materials used in the preparation of examples of coated wipes are listed in Table 1:

TABLE 1

| Material | Description |
|---|---|
| Aminoguanidine sulfate | aminoguanidine sulfate, obtained from Alfa Aesar, Ward Hill, PA |
| Benzophenone | Benzophenone, Sigma-Aldrich Co., Milwaukee, WI |
| Benzyl bromide | Benzyl bromide, obtained from Sigma-Aldrich Co |
| BUDGE | Butanedioldiglycidylether, obtained from TCI America, Portland, OR |
| t-Butanol | t-Butanol, obtained from Sigma-Aldrich Co. |
| Cellulose cloth | A cellulose based nonwoven cloth having a basis weight of 48.5 grams/meter$^2$, obtained from Suominen Corporation, Windsor Locks, CT, product code WL 102010 |
| Concentrated HCl | Concentrated hydrochloric acid, obtained from EMD Chemicals, Philadelphia, PA |
| Diacetoneacrylamide | Diacetoneacrylamide, obtained from Alfa Aesar, Ward Hill, PA |
| Dicyclohexylcarbodiimide | Dicyclohexylcarbodiimide, obtained from Alfa Aesar, Ward Hill, PA |
| IPA | 2-propanol, obtained from EMD Chemicals, Philadelphia, PA |
| Methylenebisacrylamide | Methylenebisacrylamide, obtained from Sigma-Aldrich Co. |
| O-Methylisourea hemisulfate | O-Methylisourea hemisulfate, obtained from Alfa Aesar. |
| PEI | Polyethylenimine, Catalog # 00618, 70,000 MW, 30% w/w solution in water, obtained from Polysciences, Warrington, PA |
| SCOTCH-BRITE cloth | An absorbent nonwoven counter cloth, obtained from 3M Co., St. Paul, MN, under the trade designation "SCOTCH-BRITE ABSORBENT COUNTER CLOTH" |
| SONTARA 8005 | A polyethyleneterephthalate ("PET") nonwoven wipe, obtained from DuPont Co., Wilmington, DE, under the trade designation "SONTARA 8005" |

Comparative Examples 1 to 4 (C1 to C4)

For each of Comparative Examples 1 to 4, a sample of Sontara 8005 PET nonwoven material (ca. 20 cm by 25 cm) was used, without addition of a coating material of the present disclosure.

Comparative Example 5 (C5): PEI Coated Nonwoven Wipe

Comparative Example 5 includes a PET nonwoven material coated with a polyethyleneimine polymer but without guanidinyl functionalization. A sample of polyethyleneimine, 70,000 MW (16.7 grams of a 30% by weight solution in water) was diluted to a total of 500 grams with deionized water. BUDGE (2.35 grams) was diluted to a total of 500 grams with deionized water, mixed thoroughly, then added to the PEI solution, and the mixture mixed thoroughly. This coating solution was poured into a rectangular glass dish and used to coat sheets of nonwoven material (SONTARA 8005) by a procedure similar to that described in Example 1 (see below). The coated sheets were dried, then washed and dried as described in Example 1 (see below).

Comparative Example 6 (C6)

Comparative Example 6 was a sample of cellulose sponge material (obtained from 3M Co., St. Paul, Minn., under the trade designation "SCOTCH-BRITE ABSORBENT COUNTER CLOTH"), without addition of a coating material of the present disclosure.

Comparative Example 7 (C7)

Comparative Example 7 was a sample of cellulose nonwoven cloth, without addition of a coating material of the present disclosure.

Example 1 (Ex. 1): 25% Guanylated Polyethyleneimine ("G-PEI") Coated Nonwoven Wipe Polyethylenimine, 70,000 MW (658.2 grams of a 30 wt. % solution in water, 4.59 amine equivalents) was charged to a 3 L 3-necked round bottom flask equipped with overhead stirring. O-methylisourea hemisulfate (141.2 grams, 1.15 equivalents) was charged to a 1 L beaker, and enough deionized water was added to bring the total weight to 652.8 grams. The contents of the beaker were stirred magnetically until all of the O-methylisourea hemisulfate dissolved, then the solution was poured into the round bottom flask. The reaction mixture was allowed to stir at ambient temperature overnight (about 22 hours). Analysis by NMR spectroscopy indicated conversion to the desired product. Percent solids was determined using an Ohaus moisture balance (Model Number MB35, obtained from Ohaus Corp., Parsippany, N.J.), and found to be 25.3 wt. %.

A sample of the G-PEI solution prepared as above (19.79 grams of a 25.3 wt. % solids solution) was diluted to a total of 1000 grams with deionized water. BUDGE (2.35 grams) was added and the mixture was mixed thoroughly. The solution was poured into a rectangular glass dish. Sheets of a PET nonwoven material, SONTARA 8005 (ca. 20 cm by 25 cm), were placed into the dish and submerged in the coating bath using a plastic beaker until they appeared to be thoroughly wetted with solution. The G-PEI coated nonwoven material was placed between two sheets of polyester film and a 2.28 kilogram roller was rolled over them to remove excess coating solution. The G-PEI coated nonwoven sheets were then removed from the liners and placed in trays to air dry. The G-PEI coated nonwoven sheets were individually placed into 1 gallon polyethylene jars, rinsed with deionized water, then allowed to soak in deionized water overnight. The wash water was poured off, the G-PEI coated nonwoven sheets were rinsed with deionized water again, and placed on trays to air dry. When small pieces of the G-PEI coated nonwoven sheets were placed into an aqueous solution of fluorescein disodium salt (0.01 wt. %), they were stained a deep orange-red color. In contrast, nonwovens sheets lacking the G-PEI coating gave no color change when treated with the fluorescein disodium salt.

Example 2 (Ex. 2): Poly(Diacetoneacrylamide Guanylhydrazone) ("DA") Grafted Nonwoven Wipe Diacetoneacrylamide (50 grams), methylenebisacrylamide (1 gram), and benzophenone (2.5 grams) were dissolved in methanol and diluted to a total solution weight of 500 grams. The solution was poured into a rectangular glass dish. Sheets of nonwoven material, SONTARA 8005 (ca. 20 cm by 25 cm), were pre-wet with ethanol, then soaked in the monomer solution for 1 minute, sandwiched between two sheets of polyester film and a 2.28 kilogram roller was rolled over them to remove excess coating solution. Ultraviolet ("UV") grafting was conducted using a UV stand (obtained from Classic Manufacturing, Inc., Oakdale, Minn., equipped with 18 bulbs (SYLVANIA RG2 40 W F40/350BL/ECO bulbs, 10 bulbs above and 8 bulbs 3.5 cm below the substrate, 117 cm long, spaced 5.1 cm on center), with an irradiation time of 15 minutes. After grafting, the grafted nonwoven sheets were washed for 45 minutes each with 0.9% saline, 0.9% saline, and deionized water. The DA grafted nonwoven sheets were then placed into a polyethylene bottle containing aminoguanidine sulfate (246 grams) and concentrated hydrochloric acid (5 mL) in 2 liters of deionized water, and allowed to mix on a roller over the weekend. The DA grafted nonwoven sheets were washed again as described above and allowed to dry. When small pieces of the DA grafted nonwoven sheets were placed into an aqueous solution of fluorescein disodium salt (0.01% w/w), they were stained a deep orange-red color.

Example 3 (Ex. 3): 25% Guanylated, 10% Benzylated PEI ("BG-PEI") Coated Nonwoven Wipe A 25% G-PEI solution prepared as above (300 grams of solution, 25.3 wt. % in water; the weight percentage was relative to amine equivalent weight) was charged to a 1 L round bottom flask. Benzyl bromide (19.74 grams) was dissolved in methanol to provide a total of 300 grams of solution, and this solution was then added to the round bottom flask. The flask was attached to a rotating mixer and immersed in a water bath maintained at 30° C. for 5 hours. Analysis by NMR indicated complete conversion to the desired product. A total of 339 grams of solvent was then stripped from the reaction mixture under vacuum, and 121 grams of deionized water was added to the resultant mixture. Percent solids was determined using an Ohaus moisture balance, and found to be 23.7 wt. % solids.

A sample of the BG-PEI solution prepared as above (21.1 grams of a 23.7 wt. % solids solution) was diluted to a total of 500 grams with deionized water. BUDGE (2.35 grams) was added to 500 g of deionized water and the mixture was mixed thoroughly. The two solutions were combined, mixed thoroughly, and poured into a rectangular glass dish. Sheets of a PET nonwoven material, SONTARA 8005 (ca. 20 cm by 25 cm), were placed into the dish and submerged in the coating bath using a plastic beaker until they appeared to be thoroughly wetted with solution. The BG-PEI coated nonwoven material was placed between two sheets of polyester film and a 2.28 kilogram roller was rolled over them to remove excess coating solution. The BG-PEI coated nonwoven sheets were then removed from the liners and placed in trays to air dry. The BG-PEI coated nonwoven sheets were individually placed into 1 gallon polyethylene jars, rinsed with deionized water, then allowed to soak in deionized water overnight. The wash water was poured off, and the BG-PEI coated nonwoven sheets were rinsed with deionized water again, and placed on trays to air dry. When small pieces of the BG-PEI coated nonwoven sheets were placed into an aqueous solution of fluorescein disodium salt (0.01% w/w), they were stained a deep orange-red color. In contrast, nonwovens sheets lacking the coating gave no color change when treated with the fluorescein disodium salt.

Example 4 (Ex. 4): 25% p-Chlorophenylbiguanidinyl PEI (25% CPB-PEI) Coated Nonwoven Wipe Preparation of N— [N-(4-chlorophenyl)carbamimidoyl] pyrazole-1-carboxamidine hydrochloride. A 1-L round bottom flask was charged with 1-(4-chlorophenyl)-3-cyanoguanidine (24.2 g, 125 mmol, prepared according to the procedure in Hill et al., *J. Org. Chem.*, 1984, 49, 1819-1823) and 250 mL of dioxane. The mixture was heated to about 50° C. and then treated with pyrazole (8.50 g, 125 mmol) and 31.3 mL of 4N HCl in dioxane (125 mmol). The flask was equipped with a condenser and the reaction temperature was increased to 120° C. At this point all of the starting material had dissolved. The temperature was maintained at 120° C. and a solid white mass formed soon after. Heating was continued for 1 h and then the reaction was cooled. The white solid was broken up with a spatula and then isolated by filtration. The material was washed with THF and then transferred to a round bottom flask. The material was then dried under reduced pressure to give N—[N-(4-chlorophenyl)carbamimidoyl]pyrazole-1-carboxamidine hydrochloride (33.1 g) as a white powder.

Polyethylenimine, 70,000 MW (10.0 grams of a 30% w/w solution in water, 156 mmol amine equivalents) was charged to a 250 mL round bottom flask equipped with a magnetic stirbar. Deionized water (100 mL) was added followed by the N—[N-(4-chlorophenyl)carbamimidoyl]pyrazole-1-carboxamidine hydrochloride (5.21 g, 17.4 mmol) prepared as above. The reaction mixture was heated to 100° C. and stirred under nitrogen overnight. The milky reaction mixture was then cooled, diluted to 300 mL with deionized water and transferred to a 1 liter polyethylene jar. A 46 cm by 122 cm sheet of SONTARA 8005 PET nonwoven material was then placed in the jar. A solution of BUDGE (1.41 g, 6.98 mmol), diluted to 300 mL with deionized water was then added and the polyethylene bottle was shaken vigorously for 2 minutes to thoroughly coat the nonwoven sheet. The coated nonwoven sheet was removed and carefully squeezed to remove excess coating solution. The coated nonwoven sheet was then folded in the opposite direction and returned to the polyethylene jar and shaken for an additional 2 min. Again, the coated nonwoven sheet was removed and carefully squeezed to remove excess coating solution. After being allowed to air dry overnight, the CPB-PEI coated nonwoven sheet was placed in a 1-L polyethylene jar and washed with 1 L of deionized water, with vigorous shaking, for 30 min. The water was removed and the washing procedure was repeated. The CPB-PEI coated nonwoven sheet was then carefully squeezed dry and allowed to air dry.

Example 5 (Ex. 5): 25% N,N'-Dicyclohexyl Guanylated PEI ("DCHG-PEI") Coated Nonwoven Polyethylenimine, 70,000 MW (22.2 grams of a 30 wt. % solution in water, 156 mmol amine equivalents) was charged to a 250 mL round bottom flask equipped with a magnetic stirbar. Dicyclohexylcarbodiimide (8.0 grams, 39 mmol) was added followed by 80 mL of t-butanol. The reaction was heated to 80° C. and stirred under nitrogen overnight. The reaction mixture was then cooled and concentrated under reduced pressure. The resulting syrup was concentrated from ethanol several times to give product as a milky syrup. Analysis by NMR spectroscopy indicated essentially complete conversion to the desired product. The polymer was then diluted with IPA (159 mL) to give a solution calculated to be 8.5% solids.

DCHG-PEI (5.0 g, calculated to be 5.6 mmol of amine equivalents) was diluted to 25 g with IPA in an 8 oz jar. A solution of BUDGE (118 mg), diluted to 25 g in IPA was then added and the mixture was mixed thoroughly. Three 20 cm by 20 cm sheets of SONTARA 8005 PET nonwoven material were then placed in the jar and the jar was capped with a Teflon-lined screw cap. The jar was shaken vigorously for two minutes. The DCHG-PEI coated nonwoven sheets were removed and carefully squeezed to remove excess coating solution. After being allowed to air dry overnight, the DCHG-PEI coated nonwoven sheets were placed into a 32 oz. polyethylene jar and washed in IPA, with vigorous shaking, for 15 min. The washing procedure was repeated with 1:1 IPA/deionized water and a final wash with deionized water. The DCHG-PEI coated nonwoven sheets were then allowed to air dry overnight.

Example 6 (Ex. 6): G-PEI Coated Nonwoven Wipe

Example 6 was a repeat run of making a G-PEI coated wipe, according to the details in Example 1.

Example 7 (Ex. 7): 25% Guanylated G-PEI Coated Sponge Cloth

Sheets of sponge cloth (17 cm×20 cm, SCOTCH-BRITE Absorbent Counter Cloths, available from 3M Co., St. Paul, Minn.) were individually placed into 2000 mL polyethylene bottles filled with deionized water. The bottles were sealed and placed on a shaker for 1 hour. The water was poured off. This washing procedure was repeated five more times, then the washed sponge cloths were allowed to air dry.

A coating solution was prepared as described in Example 1 from G-PEI, BUDGE, and deionized water. The washed and dried sponge cloths were coated and washed as described in Example 1.

Example 8 (Ex. 8): 25% Guanylated G-PEI Coated Cellulose Cloth

Sheets of a cellulose based nonwoven material having a basis weight of 48.5 grams/meter$^2$ (available from Suominen Corporation, Windsor Locks, Conn., product code WL 102010) were coated according to the procedure used in Example 1, to obtain a G-PEI coated cellulose cloth.

Test Method for Removal of Microorganisms from a Microorganism-Contaminated Surface and Transfer Contamination Materials used in the "Test Method for Removal of Microorganisms from a Microorganism-contaminated surface and Transfer Contamination" are listed in Table 2:

TABLE 2

Materials
*C. sporogenes* spores ATCC# 3584, titer ~1.0 × 10$^8$ CFU/mL (in water).
1x phosphate buffered saline with 0.05% TWEEN 20 ("sampling solution")
Fetal bovine serum ("FBS")
9 Medical grade stainless steel plates (304 grade), 12.7 cm by 18 cm
0.525% sodium hypochlorite in water
Isopropyl alcohol ("IPA"), 70% v/v in water
MILLI-Q deionized water
Neutralizing broth (LETHEEN BROTH, obtained from Difco, BD)
Lab paper towels
1.5 mL centrifuge tubes
3M AC PETRIFILM, obtained from 3M Co., St. Paul, MN
3 polytetrafluoroethylene ("PTFE") applicators ("dowel rods")
Snap-off swabs (CLEANTIPS Swabs)
50 mL FALCON tubes
Heating block
Wiping device (see FIGS. 4A-4B and the description in step 9 below)

The "Test Method for Removal of Microorganisms from a Microorganism-contaminated Surface and Transfer Contamination" was performed using the following protocol:

1) A stock solution of *C. sporogenes* spores (ATCC #3584) was titered on the day of the experiment to ensure that the titer was about 1×10$^8$ CFU/mL.

2) An "inoculum solution" was prepared by pipetting 500 microliters of FBS into 8.5 mL of distilled water to obtain a 9.0 mL of diluted FBS solution, and then pipetting 1.0 mL of the spore stock into the diluted FBS solution.

3) An "inoculum control sample" was prepared by pipetting 100 microliters of the inoculum solution into a 50 mL conical tube containing 10 mL of LETHEEN broth (Difco, BD). The 50 mL conical tube was sonicated for 1 minute and then vortexed for 1 minute. A 2 mL aliquot was removed and heat shocked for 10 minutes at 80° C. A 1 mL aliquot of the cells in neutralizing broth was pipetted onto a 3M PETRIFILM Aerobic Count (AC) plate. Next, a dilution series from 1:10 to 1:100,000 of the cells in neutralizing broth was prepared using sterile Butterfield's buffer (3M, 9 mL flip top tubes), and then 1 mL of each dilution was plated onto appropriately labeled AC plates.

4) Step 3 was repeated two more times, to provide a total of n=3 "inoculum control samples".

5) Three "contaminated plates" were generated for verification of microorganism recovery. The plates were contaminated by pipetting 100 mL of the inoculum solution onto each of three cleaned medical grade stainless steel plates (see the "Cleaning procedure for medical grade stainless steel plates", below). The inoculum solution was spread over the plates with PTFE dowels, and then was allowed to air dry.

Cleaning Procedure for Cleaning Medical Grade Stainless Steel Plates:
(a) About 5 mL of distilled water was pipette over the plates, and the plates were wiped clean (all wiping was done with lab paper towels);
(b) The plates were sprayed with a 1:10 dilution of household bleach in water, and after 10 minutes the plates were wiped clean;

(c) 5 mL of sterile distilled water was pipette onto the plates, and the plates were wiped clean;
(d) The plates were sprayed with 70% IPA in water and immediately wiped clean;
(e) The plates were again sprayed with 70% IPA in water and then allowed to air dry; and
(f) The plates were autoclaved at 121° C. for 20 minutes.

6) To verify recovery of microorganisms from contaminated plates, "recovery verification control" samples were obtained using a "swab recovery procedure" as described below:

Swab Recovery Procedure (Using a Single Swab for Each Plate):
(a) A snap-off swab was soaked in "sampling solution";
(b) the plate surface was swabbed diagonally twice (back and forth, switching sides of the swab between each direction);
(c) the plate surface was swabbed horizontally twice (back and forth, switching sides of the swab between each direction); and
(d) the plate surface was swabbed vertically twice (back and forth, switching sides of the swab between each direction).

The head of the swab was snapped off and placed into a 50 mL conical tube containing 10 mL of neutralizing broth. The conical tube was sonicated for 1 minute in an ultrasonic bath, followed by 1 minute of vortexing. A 2 mL aliquot was removed and heat shocked for 10 minutes at 80° C. A 1 ml sample of cells in neutralizing broth was pipette onto a 3M PETRIFILM AEROBIC COUNT (AC) plate. A dilution series from 1:10 to 1:100,000 was prepared using sterile Butterfield's buffer (9 ml flip top tubes, available from 3M Co., St. Paul, Minn.,) and 1 ml of each dilution was plated onto appropriately labeled AC plates. These were the recovery verification controls (n=3).

7) To assess the ability of a wipe to remove microorganisms from a microorganism-contaminated surface, three more "contaminated plates" were generated (using cleaned medical grade stainless steel plates, and according to the details in Step 5 above).

8) A "wet wipe" sample was generated by loading with distilled and sterile water at desired loading weight (3.5× the weight of the dry wipe). Loading technique included pipetting desired amount of deionized $H_2O$ onto the wipe, followed by gentle massaging to better incorporate the water throughout the wipe. Wipes were weighed before and after loading to ensure loading weight was correct.

Figure 4A:
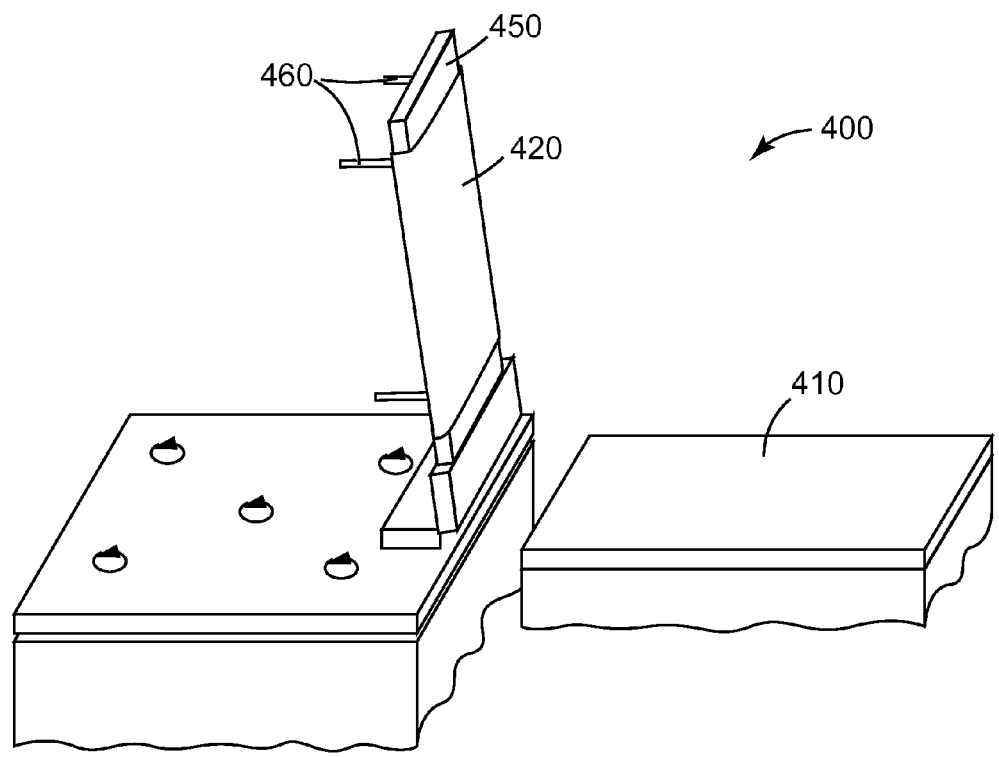
FIGS. 4A and 4B are schematic views of a mechanical wiping device used in testing wipes of the present disclosure.
Figure 4B:
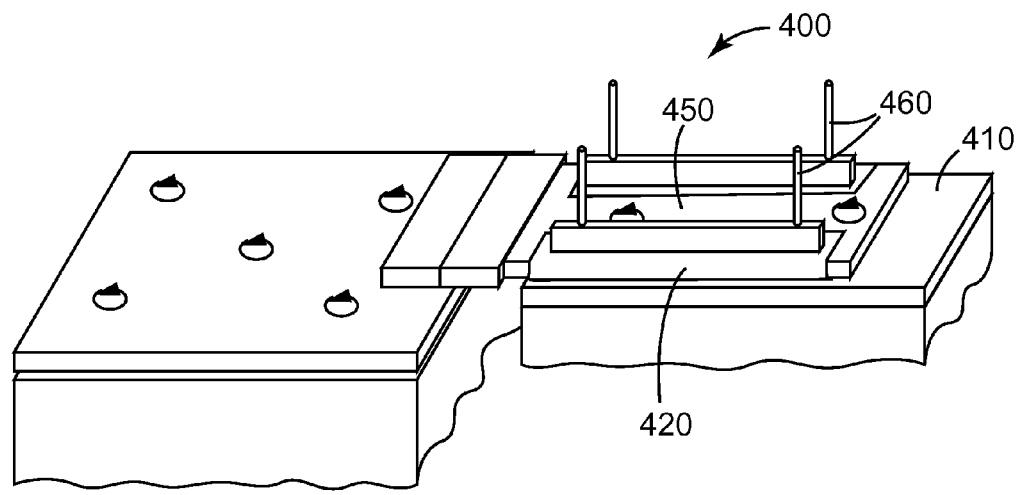

9) The wet wipe was tested using a mechanical wiping device 400 (refer to FIGS. 4A and 4B). The wet wipe 420 was locked onto the lever arm 450 of the mechanical wiping device 400 using screw clamps 460. The lever arm 450 had a mass of about 350 g. The lever arm 450 with wet wipe 420 attached was placed onto one of the contaminated plates (not shown) on platform 410. The mechanical wiping device 400 was switched on, with the lever arm 450 operating at a rotational speed of about 100 rpm (see rotation arrow in FIG. 4B) to wipe the surface of contaminated plate for 15 seconds, and the wet wipe 420 was then removed from the "wiped plate". For each type of wipe, this step was repeated to give n=3 wiped plates.

10) Each of the "wiped plates" was then swabbed according to the details in Step 6 above, to generate "removal performance" samples (n=3).

11) "Transfer contamination" samples were generated by using the wipe of Step 9, after wiping a contaminated plated, and while still attached to the arm of the mechanical wiping device, to then wipe a clean plate (see above for "Cleaning procedure for cleaning medical grade stainless steel plates") for 15 seconds at about 100 rpm. Theses wiped plates were swabbed according the details in Step 6 above, to generate the "transfer contamination" samples (n=3).

12) For any additional wipe samples, Steps 8 to 11 were repeated.

13) All dilution plates were placed in an anaerobic incubator at 37° C. for about 24 hours.

14) The plates were subjected to counting of the microorganisms and the counting data was analyzed using a $\log_{10}$ difference between recovery controls and removal performance to calculate log reductions (LRV).

Calculation of Log Reduction Value (LRV) and Standard Deviation Values ($S_{LR}$):

A "log reduction value" (LRV) is a mathematical term used here to represent the performance of a wipe in removing spores from a surface. LRV was calculated according to Equation (1) as the difference in the mean log colony (MLC) forming units between the "recovery control" ($MLC_{RC}$; this represents the initial spore population on the plates) and the remaining spores on a plate "after wiping" ($MLC_{AW}$; this represents the final spore population on the plates):

$$LRV = MLC_{RC} - MLC_{AW} \qquad \text{Equation (1):}$$

A "percent removal" value for the percent removal of microorganisms from a plate after wiping could be calculated from the LRV according to Equation (2):

$$\text{"percent removal"} = 100 \times 10^{(2-LRV)} \qquad \text{Equation (2):}$$

Thus, for example, an LRV of 3 would result in $100-10^{-1}$, or 99.9, for the corresponding percent removal value.

The variation for LRV (i.e., for LRV obtained according to Equation (1) above) was calculated as the "standard deviation of the LRV" ($S_{LR}$). Equation (3) shows the formula used to calculate $S_{LR}$, where $S_{RC}$ and $S_{AW}$ denote the standard deviation for $MLC_{RC}$ (MLC recovery control) and $MLC_{AW}$ (MLC after wiping), respectively. The number of replicates for the recovery control and the spores remaining on the surface of a plate after wiping was indicated by $n_{RC}$ and $n_{AW}$, respectively.

$$S_{LR} = [(S^2_{RC}/n_{RC}) + (S^2_{AW}/n_{AW})] \qquad \text{Equation (3):}$$

Calculation of Percent Transferred (PT):

In addition to the LRV, a percent transferred (PT) was calculated to represent the transfer of spores from a contaminated wipe (i.e., a wipe that had contacted a contaminated surface) to a new, clean surface. First, the value for "total number of spores in the wipe" (W) was calculated according to Equation (4) as the difference between the colony forming units of the "initial spore population on the plate" (I) and the "spores remaining on the plate after wiping" (R).

$$W = I - R \qquad \text{Equation (4):}$$

The "percent of spores transferred from the wipe to another surface" (PT) was then calculated according to Equation (5) (i.e., dividing the "spores recovered from a new surface after wiping with the contaminated wipe" (T) by the "total number of spores in the wipe" (W) and multiplying by 100).

$$PT = (T/W) * 100 \qquad \text{Equation (5):}$$

Using the above "Test Method for Removal of Microorganisms from a Microorganism-contaminated surface and Transfer Contamination", results for removal and cross-contamination of *C. sporogenes* ATCC #3584 spores from surfaces using cationic polymer coated wipes were summarized as in Table 3.

The Experiments (Exp. 1 to Exp. 6) were listed in Table 3 to indicate which comparative examples and the examples were tested on the same day.

Abbreviations and notes in Table 3 include the following: BG-PEI=benzyl guanylated PEI; C=control; Cel=a cellulose based nonwoven cloth; CelS=SCOTCH-BRITE ABSORBENT COUNTER CLOTH; CHG-PEI=chlorohexidine gluconate PEI; DA=poly(diacetoneacrylamide guanylhydrazone); DCHG-PEI=N,N'-dicyclohexyl guanylated PEI; Ex.=example; Exp.=experiment; G-PEI=guanylated PEI; LRV=log reduction value; NA=not available; PEI=poly(ethyleneimine); PET=poly(ethyleneterephthalate). Footnote "a": recovery control is for an amount of spores recovered from surface without wiping. Footnote "b": Values are an average (n=3, unless noted otherwise). Footnote "c": Standard deviations are listed in parenthesis (n=3, unless noted otherwise). Footnote "d": values are an average for n=2.

TABLE 3

| Experiment | Wipe Sample | Wipe Coating | Wipe Substrate | Wipe pre-loaded with water (X times weight of wipe) | Recovery control[a] ($Log_{10}$ cfu/plate) | Spores removed from surface (LRV) | Percent removal of spores from surface | Spore transferred from contaminated wipe to another, clean surface (% transferred[b]) |
|---|---|---|---|---|---|---|---|---|
| Exp. 1 | C1 | None | PET | 3.5 | 6.01 (0.06)[c] | 1.39 (0.15)[d] | 95.93 | 3.85[d] |
| Exp. 1 | Ex. 1 | G-PEI | PET | 3.5 | 6.01 (0.06) | 3.24 (0.12) | 99.94 | 0.03 |
| Exp. 1 | Ex. 2 | DA | PET | 3.5 | 6.01 (0.06) | 3.47 (0.03) | 99.97 | 0.01 |
| Exp. 2 | C2 | None | PET | 3.5 | 6.11 (0.09) | 1.60 (0.12) | 97.49 | 2.68 |
| Exp. 2 | Ex. 3 | BG-PEI | PET | 3.5 | 6.11 (0.09) | 2.58 (0.33) | 99.74 | 0.04 |
| Exp. 2 | Ex. 4 | CPB-PEI | PET | 3.5 | 6.11 (0.09) | 2.91 (0.14) | 99.88 | 0.07 |
| Exp. 3 | C3 | None | PET | 3.5 | 6.37 (0.05) | 1.39 (0.03) | 95.93 | 3.24 |
| Exp. 3 | Ex. 5 | DCHG-PEI | PET | 3.5 | 6.37 (0.05) | 3.03 (0.17) | 99.91 | 0.04 |
| Exp. 4 | C4 | None | PET | 3.5 | 6.12 (0.06) | 2.51 (0.12) | 99.69 | 0.42 |
| Exp. 4 | C5 | PEI | PET | 3.5 | 6.12 (0.06) | 2.38 (0.05) | 99.58 | 0.22 |
| Exp. 4 | Ex. 6 | G-PEI | PET | 3.5 | 6.12 (0.06) | 3.41 (0.13) | 99.96 | 0.02 |
| Exp. 5 | C6 | None | CelS | 3.5 | 6.38 (0.05) | 2.32 (0.06) | 99.52 | NA |
| Exp. 5 | Ex. 7 | G-PEI | CelS | 3.5 | 6.38 (0.05) | 3.44 (0.20) | 99.96 | NA |
| Exp. 6 | C7 | None | Cel | 4.5 | 6.28 (0.08) | 1.64 (0.04) | 97.71 | NA |
| Exp. 6 | Ex. 8 | G-PEI | Cel | 4.5 | 6.28 (0.08) | 2.59 (0.07) | 99.74 | NA |

Other modifications and variations to the present disclosure may be practiced by those of ordinary skill in the art, without departing from the spirit and scope of the present disclosure. It is understood that aspects of the various embodiments may be interchanged in whole or part or combined with other aspects of the various embodiments. The preceding description, given in order to enable one of ordinary skill in the art to practice the claimed disclosure, is not to be construed as limiting the scope of the disclosure, which is defined by the claims and all equivalents thereto.

What is claimed is:

1. A method of removing microorganisms from a microorganism-contaminated surface, the method comprising:
providing a wipe comprising:
a substrate comprising a sponge, a woven fabric, or a nonwoven fabric; and
a cationic coating disposed on a surface of the substrate, distributed throughout at least a portion of the substrate, or both, the cationic coating comprising a guanidinyl-containing polymer that is crosslinked on the substrate, covalently bonded to the substrate, or both; and
contacting the wipe in the presence of a liquid with an area of the microorganism-contaminated surface, wherein the microorganism-contaminated surface is a solid surface, wherein at least 99 percent of the microorganisms are removed from the area, and wherein the wipe, when contacted in the presence of the liquid with the area of the microorganism-contaminated surface and then contacted with a second surface, transfers no more than 0.2 percent of the microorganisms from the wipe to the second surface, wherein the guanidinyl-containing polymer is of the Formula (I):

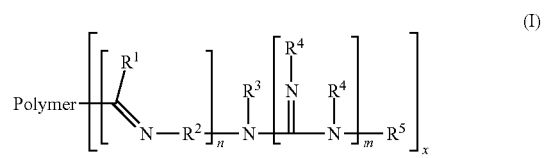

wherein:
$R^1$ is hydrogen, $C_1$-$C_{12}$ (hetero)alkyl, or a $C_5$-$C_{12}$ (hetero)aryl;
$R^2$ is a covalent bond, a $C_2$ to $C_{12}$ (hetero)alkylene, or a $C_5$-$C_{12}$ (hetero)arylene;
$R^3$ is hydrogen, $C_1$-$C_{12}$ (hetero)alkyl, or $C_5$-$C_{12}$ (hetero)aryl;
each $R^4$ is independently hydrogen, $C_1$-$C_{12}$ (hetero)alkyl, $C_5$-$C_{12}$ (hetero)aryl;
$R^5$ is hydrogen, $C_1$-$C_{12}$ (hetero)alkyl, or $C_5$-$C_{12}$ (hetero)aryl, or $N(R^4)_2$;
n is 0 or 1;
m is 1 or 2; and
x is an integer equal to at least 1.

2. The method according to claim 1, wherein n=0.

3. The method according to claim 1, wherein n=1.

4. The method according to claim 1, wherein the guanidinyl-containing polymer is present in an amount of 0.1 weight percent to 10 weight percent based on a total weight of the wipe.

5. The method according to claim 1, wherein the liquid comprises water, a water-miscible organic solvent, or a mixture thereof.

6. The method according to claim 1, wherein the guanidinyl-containing polymer comprises a carbonyl-containing polymer precursor or an amino-containing polymer precursor.

7. The method according to claim 1, wherein the microorganisms comprise spores.

8. The method according to claim 1, wherein the microorganisms comprise bacterial endospores.

9. The method according to claim 1, wherein the substrate is formed of a material selected from poly(meth)acrylates, poly(meth)acrylamides, polyolefins, poly(isoprenes), poly(butadienes), fluorinated polymers, chlorinated polymers, polyamides, polyimides, polyethers, poly(ether sulfones), poly(sulfones), poly(vinyl acetates), copolymers of vinyl acetate, poly(phosphazenes), poly(vinyl esters), poly(vinyl ethers), poly(vinyl alcohols), poly(carbonates), polyurethanes, or cellulosic materials.

10. The method according to claim 2, wherein the guanidinyl-containing polymer comprises an amino-containing polymer precursor.

11. The method according to claim 2, wherein the guanidinyl-containing polymer is crosslinked with a polyglycidylether.

12. The method according to claim 3, wherein the guanidinyl containing polymer comprises a carbonyl containing polymer precursor.

13. The method according to claim 3, wherein the guanidinyl-containing polymer is crosslinked with a N,N'-(hetero)alkylenebis(meth)acrylamide.

* * * * *

UNITED STATES PATENT AND TRADEMARK OFFICE
CERTIFICATE OF CORRECTION

| | | |
|---|---|---|
| PATENT NO. | : 10,087,405 B2 | Page 1 of 2 |
| APPLICATION NO. | : 14/896145 | |
| DATED | : October 2, 2018 | |
| INVENTOR(S) | : Steven Swanson et al. | |

It is certified that error appears in the above-identified patent and that said Letters Patent is hereby corrected as shown below:

In the Specification

<u>Column 6</u>,
Line 3, delete "Polymer —N($R^3$)H." and insert -- Polymer—N($R^3$)H. --, therefor.
Lines 32 & 33, delete "amino styrene)," and insert -- aminostyrene), --, therefor.
Line 34, delete "amino ethylmethacrylate)." and insert -- aminoethylmethacrylate). --, therefor.

<u>Column 11</u>,
Line 52, delete "amino ethyl)trimethylammonium" and insert -- aminoethyl)trimethylammonium --, therefor.

<u>Column 13</u>,
Line 60, delete "Polymer —C(=O)—$R^1$." and insert -- Polymer—C(=O)—$R^1$. --, therefor.

<u>Column 15</u>,
Line 48, delete "ethylenebis (1" and insert -- ethylenebis(1 --, therefor.
Line 49, delete "decamethylenebis (1-" and insert -- decamethylenebis(1- --, therefor.

<u>Column 17</u>,
Line 55, delete "poly(l-" and insert -- poly(1- --, therefor.

<u>Column 21</u>,
Line 52, delete "anthracia," and insert -- anthracis, --, therefor.

<u>Column 30</u>,
Line 28, delete "N— [N-" and insert -- N—[N- --, therefor.

<u>Column 34</u>,
Line 28, delete "100×10" and insert -- 100-10 --, therefor.

Signed and Sealed this
Thirteenth Day of November, 2018

Andrei Iancu
*Director of the United States Patent and Trademark Office*

In the Claims

Column 36,
Line 50, in Claim 1, delete "N(R$^4$)$_2$;" and insert -- —N(R$^4$)$_2$; --, therefor.